US006458539B1

(12) United States Patent
Gold et al.

(10) Patent No.: US 6,458,539 B1
(45) Date of Patent: *Oct. 1, 2002

(54) PHOTOSELECTION OF NUCLEIC ACID LIGANDS

(75) Inventors: Larry Gold; Jonathan Drew Smith; Tad Koch, all of Boulder; Mace Golden, Highlands Ranch, all of CO (US)

(73) Assignee: Somalogic, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/619,213

(22) Filed: Jul. 19, 2000

Related U.S. Application Data

(63) Continuation-in-part of application No. 09/459,553, filed on Dec. 13, 1999, now Pat. No. 6,291,184, and a continuation-in-part of application No. 09/093,243, filed on Jun. 8, 1998, now Pat. No. 6,001,577, and a continuation-in-part of application No. 08/612,895, filed on Mar. 8, 1996, now Pat. No. 5,763,177, each is a continuation-in-part of application No. 08/123,935, filed on Sep. 17, 1993, now abandoned.

(51) Int. Cl.[7] .......................... C12Q 1/68; C12P 19/34; C07H 21/04; C07H 21/02
(52) U.S. Cl. .......................... 435/6; 435/91.2; 536/22.1; 536/23.1; 536/24.3; 536/25.4
(58) Field of Search .................. 435/6, 91.2; 536/22.1, 536/23.1, 24.3, 25.4

(56) References Cited

U.S. PATENT DOCUMENTS

| 5,035,996 A | | 7/1991 | Hartley ........................... 435/6 |
| 5,270,163 A | | 12/1993 | Gold et al. ...................... 435/6 |
| 5,475,096 A | * | 12/1995 | Gold et al. ................. 536/23.1 |
| 5,723,323 A | | 3/1998 | Kauffman et al. .............. 435/6 |
| 5,763,177 A | * | 6/1998 | Gold et al. ..................... 435/6 |

FOREIGN PATENT DOCUMENTS

| AU | 692469 | 11/1998 |
| GB | 2 183 661 A | 6/1987 |
| WO | WO 89/06694 | 7/1989 |
| WO | WO 91/19813 | 12/1991 |
| WO | WO 92/14843 | 9/1992 |
| WO | WO 93/05182 | 3/1993 |
| WO | WO 95/07364 | 3/1995 |

OTHER PUBLICATIONS

Allen et al. (1991) J. Biol. Chem. 266:6113.
Barbier et al. (1984) Biochemistry 23:2933.
Bartel and Szostak (1993) Science 261:1411.
Bayley and Knowles (1977) Methods and Enzymol. 46:69.
Beckett et al. (1988) J. Mol. Biol. 204:939.
Beaudry and Joyce (1992) Science 257:635.
Blatter et al. (1992) Nature 359:650.
Carey et al. (1983) Biochemistry 22:4723.
Chen and Prusoff (1977) Biochemistry 16:3310.
Czarnecki et al. (1979) Methods Enzymol. 56:642.
Dietz and Koch (1989) Photochem. Photobiol. 49:121.
Dietz and Koch (1987) Photochem. Photobiol. 46:971.
Dietz et al. (1987) J. Am. Chem. Soc. 109:1793–1797.
Eggen and Nathans (1969) J. Mol. Biol. 39:293.
Ellington & Szostak (1990) Abstracts of papers presented at the 1990 meeting on RNA Processing, Cold Spring Harbor Laboratory, Cold Spring Harbor, NY, p. 84.
Evans et al. (1989) Biochemistry 28:713.
Farrar et al. (1991) Biochemistry 30:3075–3082.
Favre (1990) in Bioorganic Photochemistry, vol. 1: Photochemistry and the Nucleic Acids (Morrison, H., Ed.) 379–425, John Wiley and Sons: New York.
Gott et al. (1991) Biochemistry 30:6290–6295.
Groebe and Uhlenbeck (1988) Nucleic Acids Res. 16:11725.
Hanna et al. (1993) Nucleic Acids Res. 21:2073.
Hutchinson and Kohnlein (1980) Prog. Subcell. Biol. 7:1.
Ito et al. (1980) J. Am. Chem. Soc. 102:7535.
Ito et al. (1980) Photchem. Photobiol. 32:683.
Jensen et al. (1995) Proc. Natl. Acad. of Sci. USA 92:12220–4.
Joyce (1989) Gene 82:83.
Joyce & Inoue (1989) Nucleic Acids Research 17:711.
Katouzian–Safadi et al. (1991) Photochem. Photobiol. 53:611.
Katouzian–Safadi et al. (1991) Nucleic Acids Research 19:4937–4941.
Khalili (1988) EMBO J. 7:1205.
Kinzler & Vogelstein (1989) Nucleic Acids Research 17:3645.
Kramer et al. (1974) J. Mol. Biol. 89:719.
Lee et al. (1991) J. Biol. Chem. 266:16478.
Lehman & Joyce (1993) Nature 361:182–185.
Levisohn & Spiegelman (1968) Proc. Natl. Acad. Sci. USA 60:866.
Levisohn & Spiegelman (1969) Proc. Natl. Acad. Sci. USA 63:805.
Lin and Riggs (1974) Proc. Natl. Acad. Sci. USA 71:947.
Ling et al. (1970) Virology 40:920.
Liu and Verdine (1992) Tetrahedron Letters 33:4265.
Mee (1987) in *Radiation Chemistry: Principles and Applications* 477–499 (Farhataziz and Rodgers, eds.), VCH Publishers, New York.
Milligan et al. (1987) Nucleic Acids Res. 15:8783.
Ogata and Gilbert (1977) Proc. Natl. Acad. Sci. USA 74:4973.
Oliphant & Struhl (1987) Methods in Enzymology 155:568.
Oliphant et al. (1989) Mol. Cell. Biol. 9:2944.

(List continued on next page.)

Primary Examiner—Stephanie Zitomer
(74) Attorney, Agent, or Firm—Swanson & Bratschun, LLC

(57) ABSTRACT

Methods are described for the identification and preparation of high-affinity nucleic acid ligands to bFGF. Included in the invention are specific DNA ligands to bFGF identified by the photoSELEX method. Also included is a method for determining the position of a nucleic acid ligand-protein photoadduct.

49 Claims, 15 Drawing Sheets

OTHER PUBLICATIONS

Oliphant & Struhl (1988) Nucleic Acids Research 16:7673.
Oliphant et al. (1986) Gene 44:177.
Rahn and Sellin (1982) Photochem. Photobiol. 35:459.
Rahn and Stafford (1979) Photochem. Photobiol. 30:449.
Robertson & Joyce (1990) Nature 344:467.
Rothman and Kearns (1967) Photochem. Photobiol. 6:775.
Saito et al. (1986) J. Org. Chem. 51:148.
Saito and Sugiyama (1990) in Bioorganic Photochemistry, vol. 1: Photochemistry and the Nucleic Acids, (Morrison, H., Ed.) 317–340, John Wiley & Sons: New York.
Salvucci and Haley (1990) Planta 181:287.
Schneider et al. (1992) J. Mol. Biol. 228:862.
Shetlar (1980) Photochem. Photobiol. Rev. 5:105.
Sugiyama et al. (1993) J. Amer. Chem. Soc. 115:4443.
Szostak (1988) "Structure and Activity of Ribozymes," in Redesigning the Molecules of Life, (S.A. Benner ed.) Springer–Verlag Berline Heidelberg, pp. 87–113.
Szybalski (1974) Cancer Chemother. Rep. 58:539.
Talbot et al. (1990) Nucleic Acids Res. 18:3521.
Tanner et al. (1988) Biochemistry 27:8852.
Thiesen & Bach (1990) Nucleic Acids Research 18:3203.
Tuerk & Gold (1990) Science 249:505–510.
Weber (1967) Biochemistry 6:3144.
Weintraub (1973) Cold Spring Harbor Symp. Quant. Biol. 38:247.
Wick and Matthews (1991) J. Biol. Chem. 266:6106.
Wolfes et al. (1986) Eur. J. Biochem. 159:267.
Wower et al. (1989) Biochemistry 28:1563.
Wower et al. (1988) Biochemistry 27:8114.
Wyatt et al. (1992) Genes & Development 6:2542.

* cited by examiner sequence 06.50
gggaggacgatgcggTGACGTAAGAGTGTAATCGATGCAGCCTGGcagacgacgagcggga
SEQ ID NO:70 sequence 06.15
gggaggacgatgcggGCGAAGGCACACCGAGTTCATAGTATCCCAcagacgacgagcggga
SEQ ID NO:76

US 6,458,539 B1

PHOTOSELECTION OF NUCLEIC ACID LIGANDS

RELATED APPLICATIONS

This application is a continuation-in-part of U.S. patent application Ser. No. 09/459,553, filed Dec. 13, 1999, which is a divisional of U.S. patent applicaton Ser. No. 09/093,293, filed Jun. 8, 1998, now U.S. Pat. No. 6,001,577 and is a continuation-in-part of U.S. patent application Ser. No. 08/612,895, filed Mar. 8, 1996, now U.S. Pat. No. 5,763,177, each of which is entitled "Systematic Evolution of Ligands by Exponential Enrichment: Photoselection of Nucleic Ligands and Solution SELEX." U.S. patent application Ser. No. 09/459,553; U.S. Pat. No. 6,001,577; and U.S. Pat. No. 5,763,177, are each continuations-in-part of U.S. patent application Ser. No. 08/123,935, filed Sep. 17, 1993, entitled "Photoselection of Nucleic Acid Ligands," now abandoned.

FIELD OF INVENTION

Described herein are methods for identifying and preparing high-affinity nucleic acid ligands and nucleic acid ligands capable of photocrosslinking to target molecules specifically disclosed as nucleic acid ligands to basic Fibroblast Growth Factor$_{155}$ (bFGF$_{(155)}$). The method utilized herein for identifying such ligands is called PhotoSELEX, an acronym for Photochemical Systematic Evolution of Ligands by EXponential enrichment. This invention includes high-affinity DNA ligands capable of photocrosslinking bFGF$_{(155)}$. Specifically disclosed are two modified ssDNA ligands to bFGF$_{(155)}$ which exhibited high sensitivity for bFGF$_{(155)}$ comparable to that of commercially available ELISA monoclonal antibodies with an absolute sensitivity of at least 0.058 ppt bFGF$_{(155)}$ under prevailing test conditions. Additionally, the ligands were able to distinguish bFGF$_{(155)}$ from consanguine proteins, Vascular Endothelial Growth Factor (VEGF) and Platelet Derived Growth Factor (PDGF) and from other proteins in serum. Further included within the scope of this invention is a method for determining the exact position of the photocrosslink between the nucleic acid ligand and the target molecule. The present invention includes the use of nucleic acid ligands capable of photocrosslinking to targets as diagnostic reagents.

BACKGROUND OF THE INVENTION

Effective diagnostics capable of early and accurate detection of marker proteins and other analyte molecules is an area of research emphasis in the pharmaceutical industry. Despite the intensity of recent efforts, many diagnostic protocols still rely on immunochemical detection techniques first described in the early 1970's (Engvall and Perlman (1971) Immunochem. 8:871–874; Engvall and Perlman (1972) J. Immunol. 109:129–135; Hoffman (1973) J. Allergy Clin. Immunol. 5:303–307; Ljungstrom et al. (1974) Parasitology 69:xxiv). The major technique to evolve from these original investigations is the enzyme-linked immunosorbent assay (ELISA) with the sandwich immunoassay protocol representing the state of the art for large molecule (e.g. protein) detection.

While the sandwich ELISA has been a reliable mainstay for protein and antigen detection, it is often a costly, time consuming and labor intensive technique. Despite efforts to expand and automate the ELISA assay, no system is currently available for the detection of a wide array of important marker proteins in a patient from a single, small sample of the patient's serum or plasma. In the present research, an in vitro selection methodology called Photochemical Systematic Evolution of Ligands by Exponential Enrichment (photoSELEX) has been employed to identify oligodeoxynucleotide ligands which may supplant antibodies evolved through immunological techniques as diagnostic agents.

Selex

A method for the in vitro evolution of nucleic acid molecules with high affinity binding to target molecules has been developed. This method, Systematic Evolution of Ligands by EXponential enrichment, termed SELEX, is described in U.S. patent application Ser. No. 071536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096 and U.S. patent application Ser. No. 07/931,473, filed Aug. 17, 1992, entitled "Methods for Identifying Nucleic Acid Ligands," now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

Since its conception more than ten years ago, Systematic Evolution of Ligands by Exponential Enrichment (SELEX) has proven to be a valuable combinatorial technique. The SELEX methodology has been used to successfully identify natural, as well as, modified RNA and ssDNA ligands capable of binding with high affinity and specificity to an impressive array of target molecules (Ellington and Szostak (1990) Nature 346:818–822; Gold et al. (1995) Annu. Rev. Biochem. 64:763–799; Morris et al. (1998) Proc. Natl. Acad. Sci. (USA) 95:2902–2907; Osborne and Ellington (1997) Chem. Rev. 97:349–370; Ruckman et al. (1998) J. Biol. Chem. 273:20556–20567; Schneider et al. (1995) Biochemistry 34:9599–9610; Tuerk and Gold (1990) Science 249:505–510)).

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled "Method for Selecting Nucleic Acids on the Basis of Structure," now abandoned (see U.S. Pat. No. 5,707,796), describes the use of SELEX in conjunction with gel electrophoresis to select nucleic acid molecules with specific structural characteristics, such as bent DNA (See U.S. Pat. No. 5,707,796). U.S. patent application Ser. No. 08/123,935, filed Sep. 17, 1993, entitled "Photoselection of Nucleic Acid Ligands," now abandoned (see U.S. Pat. No. 5,763,177), describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned (see U.S. Pat. No. 55,580,737), describes a method for identifying highly specific nucleic acid ligands able to discriminate between closely related molecules, termed "Counter-SELEX." U.S. patent application Ser. No. 08/143,564, filed Oct. 25, 1993, entitled "Systematic Evolution of Ligands by EXponential Enrichment: Solution SELEX," now abandoned, (see U.S. Pat. No. 5,567,588) and U.S. patent application Ser. No. 08/792,075, filed Jan. 31, 1997, entitled "Flow Cell SELEX," now U.S. Pat. No. 5,861,254, describe SELEX-based methods which achieve highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved nucleic acid ligands after the SELEX process has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (see U.S. Pat. No. 5,660,985), that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines. PCT/US98/00589, filed Jan. 7, 1998, entitled "Bioconjugation of Oligonucleotides," (WO98/30720), describes a method for identifying bioconjugates to a target comprising nucleic acid ligands derivatized with a molecular entity exclusively at the 5'-position of the nucleic acid ligands.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. The full text of the above described patent applications, including but not limited to, all definitions and descriptions of the SELEX process, are specifically incorporated herein by reference in their entirety.

In the PhotoSELEX variation of SELEX, a modified nucleotide activated by absorption of light is incorporated in place of a native base in either RNA- or in ssDNA-randomized oligonucleotide libraries. See U.S. patent application Ser. No. 09/459,553, filed Dec. 13, 1999; U.S. Pat. Nos. 6,001,577; and 5,763,177, each entitled "Systematic Evolution of Ligands by Exponential Enrichment: Photoselection of Nucleic Ligands and Solution SELEX;" and U.S. patent application Ser. No. 08/123,935, filed Sep. 17, 1993, entitled "Photoselection of Nucleic Acid Ligands," now abandoned, each of which is specifically incorporated herein by reference in its entirety). One such modified nucleotide whose photochemistry is particularly well-suited for this purpose is 5-bromo-2'-deoxyuridine (BrdU) (Meisenheimer and Koch (1997) Crit. Rev. Biochem. Mol. Biol. 32:101–140). The 5-bromouracil chromophore absorbs ultraviolet (UV) light in the 310 nm range where native chromophores of nucleic acids and proteins do not absorb or absorb very weakly. The resulting excited singlet state intersystem crosses to the lowest triplet state which specifically crosslinks with aromatic and sulfur-bearing amino acid residues of a protein target in suitable proximity (Dietz and Koch (1987) Photochem. Photobiol. 46:971–8; Dietz and Koch (1989) Photochem. Photobiol. 49:121–9; Dietz et al. (1987) J. Am. Chem. Soc. 109:1793–1797; Ito et al. (1980) J. Am. Chem. Soc. 102:7535–7541; Swanson et al. (1981) J. Am. Chem. Soc. 103:1274–1276). Crosslinking may also occur via excitation of an aromatic residue of the protein in proximity to the bromouracil chromophore (Norris et al (1997) Photochem. Photobiol. 65:201–207). Of particular importance, excited bromouracil in DNA is relatively unreactive in the absence of a proximal, oriented, reactive amino acid (Gott et al. (1991) Biochemistry 30:6290–6295; Willis et al. (1994) Nucleic Acids Res. 22:4947–4952; Norris et al. (1997) Photochem. Photobiol. 65:201–207) or nucleotide residue (Sugiyama et al. (1990) J. Am. Chem. Soc. 112:6720–6721; Cook and Greenberg (1996) J. Am. Chem. Soc. 118:10025–10030). The importance of orientation is evident in crystal structures of protein-nucleic acid complexes which show a lock and key arrangement of the bromouracil chromophore with the aromatic amino acid residue to which it crosslinks (Horvath et al. (1998) Cell 95:963–974; Meisenheimer and Koch (1997) Crit. Rev. Biochem. Mol. Biol. 32:101–140).

Basic fibroblast growth factor (bFGF$_{(155)}$) is a 155-amino acid member of the Fibroblast Growth Factor family of polypeptides, having the following primary amino acid sequence (SEQ ID NO:99):

```
          10         20         30         40
MAAGS ITTLP ALPED GGSGA FPPGH FKDPK RLYCK NGGFF 50         60         70         80
LRIHP DGRVD GVREK SDPHI KLQLQ AEERG VVSIK GVCAN
```

```
              90             100           110            120
RYLAM  KEDGR LLASK  CVTDE  CFFFE  RLESN  NYNTY  RSRKY 130            140           150    155
TSWYV  ALKRT  GQYKL  GSKTG  PGQKA  ILFLP  MSAKS.
``` bFGF$_{(155)}$ is a multifunctional effector for many cells of mesenchymal and neuroectodermal origin (Rifkin and Moscatelli (1989) J. Cell Biol. 109:1; Baird and Bohlen (1991) in Peptide Growth Factors and Their Receptors (Spom, M. B. and Roberts, A. B., eds.); pp. 369–418, Springer, N.Y.; Basilico and Moscatelli (1992) Adv. Cancer Res. 59:115). It is one of the most studied and best characterized members of a family of related proteins that also includes acidic FGF (Jaye et al. (1986) Science 233:541; Abraham et al. (1986) Science 233:545), int-2 (Moore et al. (1986) EMBO J. 5:919), kFGF/hst/KS3 (Delli-Bovi et al. (1987) Cell 50:729; Taira et al (1987) Proc. Natl. Acad. Sci. USA 84:2980), FGF-5 (Zhan et al. (1988) Mol. Cell. Biol. 8:3487), FGF-6 (Marics et al. (1989) Oncogene 4:335) and keratinocyte growth factor/FGF-7 (Finch et aL (1989) Science 245:752).

In vitro, bFGF stimulates cell proliferation, migration and induction of plasminogen activator and collagenase activities (Presta et al. (1986) Mol. Cell. Biol. 6:4060; Moscatelli et al. (1986) Proc. Natl. Acad. Sci. USA 83:2091; Mignatti etal. (1989) J. Cell Biol. 108:671). In vivo, it is one of the most potent inducers of neovascularization. Its angiogenic activity in vivo suggests a role in tissue remodeling and wound healing, but also in some disease states that are characterized by pathological neovascularization, such as tumor proliferation, tumor metastasis, diabetic retinopathy and rheumatoid arthritis (Folkman and Klagsbrun (1987) Science 235:442; Gospodarowitz (1991) Cell Biology Reviews 25:307).

Although bFGF does not have a signal sequence for secretion, it is found on both sides of the plasma membrane, presumably being exported via exocytosis (Vlodavsky et al. (1991) Trends Biol. Sci. 16:268; Mignatti and Rifkin (1991) J. Cell. Biochem. 47:201). In the extracellular matrix, it is typically associated with a fraction that contains heparan sulfate proteoglycans. Indeed, heparin affinity chromatography has been a useful method for purification of this and other heparin-binding growth factors. In cell culture, bFGF binds to low- and high-affinity sites. The low-affinity sites are composed of cell-associated heparan sulfate proteoglycans to which bFGF binds with approximately nanomolar affinity (Moscatelli (1987) J. Cell. Physiol. 131:123). All biological effects of bFGF are mediated through interaction with the high-affinity binding sites (10–100 pM) that represent the dimeric tyrosine kinase FGF receptor (IJeno et aL (1992) J. Biol. Chem. 267:1470). Five FGF receptor genes have been identified to date, each of which can produce several structural variants as a result of alternative mRNA splicing (Armstrong et al. (1992) Cancer Res. 52:2004; Ueno et al. (1992) J. Biol. Chem. 267:1470). There is by now substantial evidence that the low- and the high-affinity binding sites act cooperatively in determining the overall affinity of bFGF. Experiments with mutant cell lines that are deficient in glycosaminoglycan synthesis (Yayon et al. (1991) Cell 64:841) or heparitinase treated cells (Rapraeger et al. (1991) Science 252:1705) have shown that binding of either cell-associated heparan sulfate or, in its absence, exogenously added heparin to bFGF is required for signaling via the tyrosine kinase receptor. Recent resolution of observed Kd into its kinetic components demonstrates that while the association rates of bFGF to the low- and the high-affinity sites are comparable, the dissociation rate of bFGF from the cell surface receptor is 23-fold slower than that for the cell-associated heparan sulfate (Nugent and Edelman (1992) Biochemistry 31:8876). The slower off-rate, however, is only observed when the receptor is bound to the cell surface suggesting that simultaneous binding to both sites contributes to the overall high-affinity binding. This is plausible in light of the observation that the heparin-binding and the receptor-binding sites are located on adjacent, but separate regions of the molecule, as determined from the recently solved X-ray crystal structure of bFGF (Zhang et al. (1991) Proc. Natl. Acad. Sci. USA 88:3446; Eriksson et al. (1991) Proc. Natl. Acad. Sci. USA 88:3441; Ago et al. (1991) J. Biochem. 110:360, Zhu et al. (1991) Science 251:90).

The idea that bFGF antagonists may have useful medicinal applications is not new (reviewed in Gospodarowicz (1991) Cell Biology Reviews 25:307). bFGF is now known to play a key role in the development of smooth-muscle cell lesions following vascular injury (Reidy et al. Circulation, Suppl. III 86:III43). Overexpression of bFGF (and other members of the FGF family) is correlated with many malignant disorders (Halaban et al. (1991) Ann. N. Y. Acad. Sci. 638:232; Takahashi et al. (1990) Proc. Natl. Acad. Sci. USA 87:5710; Fujimoto et al. (1991) Biochem. Biophys. Res. Commun. 180:386) and recently, neutralizing anti-bFGF antibodies have been found to suppress solid tumor growth in vivo by inhibiting tumor-linked angiogenesis (Hori et al. (1991) Cancer Res. 51:6180). Notable in this regard is the recent therapeutic examination of suramin, a polysulfated naphthalene derivative with known antiprotozoal activity, as an anti-tumor agent. Suramin is believed to inhibit the activity of bFGF through binding in the polyanion binding site and disrupting interaction of the growth factor with its receptor (Middaugh et al. (1992) Biochemistry 31:9016; Eriksson et al. (1991) Proc. Natl. Acad. Sci. USA 88:3441). In addition to having a number of undesirable side effects and substantial toxicity, suramin is known to interact with several other heparin-binding growth factors which makes linking of its beneficial therapeutic effects to specific drug-protein interactions difficult (La Rocca et al. (1990) Cancer Cells 2:106). Anti-angiogenic properties of certain heparin preparations have also been observed (Folkman et al. (1983) Science 221:719; Crum et al. (1985) Science 250:1375) and these effects are probably based at least in part on their ability to interfere with bFGF signaling. While the specific heparin fraction that contributes to bFGF binding is now partially elucidated (Ishai-Michaeli et al. (1992) Biochemistry 31:2080; Turnbull et aL (1992) J. Biol. Chem. 267:10337), a typical heparin preparation is heterogeneous with respect to size, degree of sulfation and iduronic acid content. Additionally, heparin also affects many enzymes and growth factors.

SUMMARY OF THE INVENTION

Described herein are the uses of photoaptamers in a diagnostic system. Photoaptamers can be evolved to numerous targets and can be used to covalently bind the target to a surface for direct detection. Use of a photoaptamer as a capture molecule in a diagnostic assay adds an extra dimension of specificity and supplants the need for sandwich assays. The photoaptamer is attached to any suitable solid support as described in U.S. patent application Ser. No. 09/561,465, filed Jun. 12, 2000 and U.S. patent application Ser. No. 08/990,436, filed Jun. 15, 1997, both entitled "Nucleic Acid Ligand Diagnostic Biochip," which are specifically incorporated herein by reference in their entirety. A sample containing unknown substances (e.g. proteins) can be applied to the solid support containing immobilized photoaptamers and an affinity association is formed if the sample contains the target for the photoaptamer. After appropriate incubation, and an optional mild wash the solid support is irradiated with UV light causing covalent bond formation between the photoaptamer and the target. Very aggressive washing can than take place (e.g. with strong detergents for denaturants) to eliminate non-specific binding. Finally, the amount of bound target can be directly determined. If the target is a protein, the detection can be made using a universal protein stain capable of conjugation to the amino acids of the covalently bound protein. Other suitable detection methods, such as SPR, are also compatible with the use of photoaptamers.

Also described herein are methods for identifying and preparing high-affinity nucleic acid ligands and nucleic acid ligands capable of photo crosslinking to target molecules specifically disclosed as nucleic acid ligands to basic Fibroblast Growth Factor$_{155}$ (bFGF$_{(155)}$). The present invention includes methods of identifying and producing nucleic acid ligands to human basic Fibroblast Growth Factor$_{155}$ (bFGF$_{(155)}$) and the nucleic acid ligands so identified and produced. In particular, DNA sequences are provided that are capable of photocrosslinking bFGF$_{(155)}$. Specifically included in the invention are the DNA ligand sequences shown in Tables 1 and 2 and FIG. 2A (SEQ ID NOS:4–98). The photocrosslinking nucleic acid ligands form tight Michaelis complexes with the targets. The photocrosslinking step enhances the specificity of the protein-nucleic acid ligand interaction.

In one variation, the method of the present invention comprises preparing a candidate mixture of nucleic acid sequences which contain photoreactive groups; contacting the candidate mixture with a target molecule wherein nucleic acid sequences having increased affinity to the target molecule bind the target molecule, forming nucleic acid-target molecule complexes; irradiating the nucleic acid-target molecule mixture, wherein some nucleic acids incorporated in nucleic acid-target molecule complexes crosslink to the target molecule via the photoreactive functional groups; taking advantage of the covalent bond to partition the crosslinked nucleic acid-target molecule complexes from free nucleic acids in the candidate mixture; and identifying the nucleic acid sequences that were photocrosslinked to the target molecule. The process can further include the iterative step of amplifying the nucleic acids that photocrosslinked to the target molecule to yield a mixture of nucleic acids enriched in sequences that are able to photocrosslink to the target molecule.

More specifically, the present invention includes the DNA ligands to bFGF$_{(155)}$ identified according to the above-described method, including those ligands shown in Tables 1 and 2 and FIG. 2A (SEQ ID NOS:4–98). Also included are nucleic acid ligands to bFGF$_{(155)}$ that are substantially homologous to any of the given ligands and that have substantially the same ability to bind bFGF$_{(155)}$. Further included in this invention are nucleic acid ligands to bFGF$_{(155)}$ that have substantially the same structural form as the ligands presented herein and that have substantially the same ability to bind bFGF$_{(155)}$.

In another variation of this embodiment of the present invention, nucleic acid sequences containing photoreactive groups are selected through SELEX for a number of rounds in the absence of irradiation, resulting in a candidate mixture with a partially enhanced affinity for the target molecule. PhotoSELEX is then conducted with irradiation to select ligands able to photocrosslink to the target molecule.

The present invention also includes an improved method for determining the position of the photocrosslink between the nucleic ligand and the target molecule. In this variation of the present invention the photocrosslinked amino acid is identified by sequencing the photo-crosslinked amino acid nucleic acid ligand complex by Mass Spectrometry and the photo-crosslinked base is identified by Maxam-Gilbert sequencing.

The present disclosure provides non-limiting examples which are illustrative and exemplary of the invention. Other partitioning schemes and methods of selecting nucleic acid ligands through binding and photocrosslinking to a target molecule will be become apparent to one skilled in the art from the present disclosure.

DETAILED DESCRIPTION OF THE INVENTION

Figure 1:
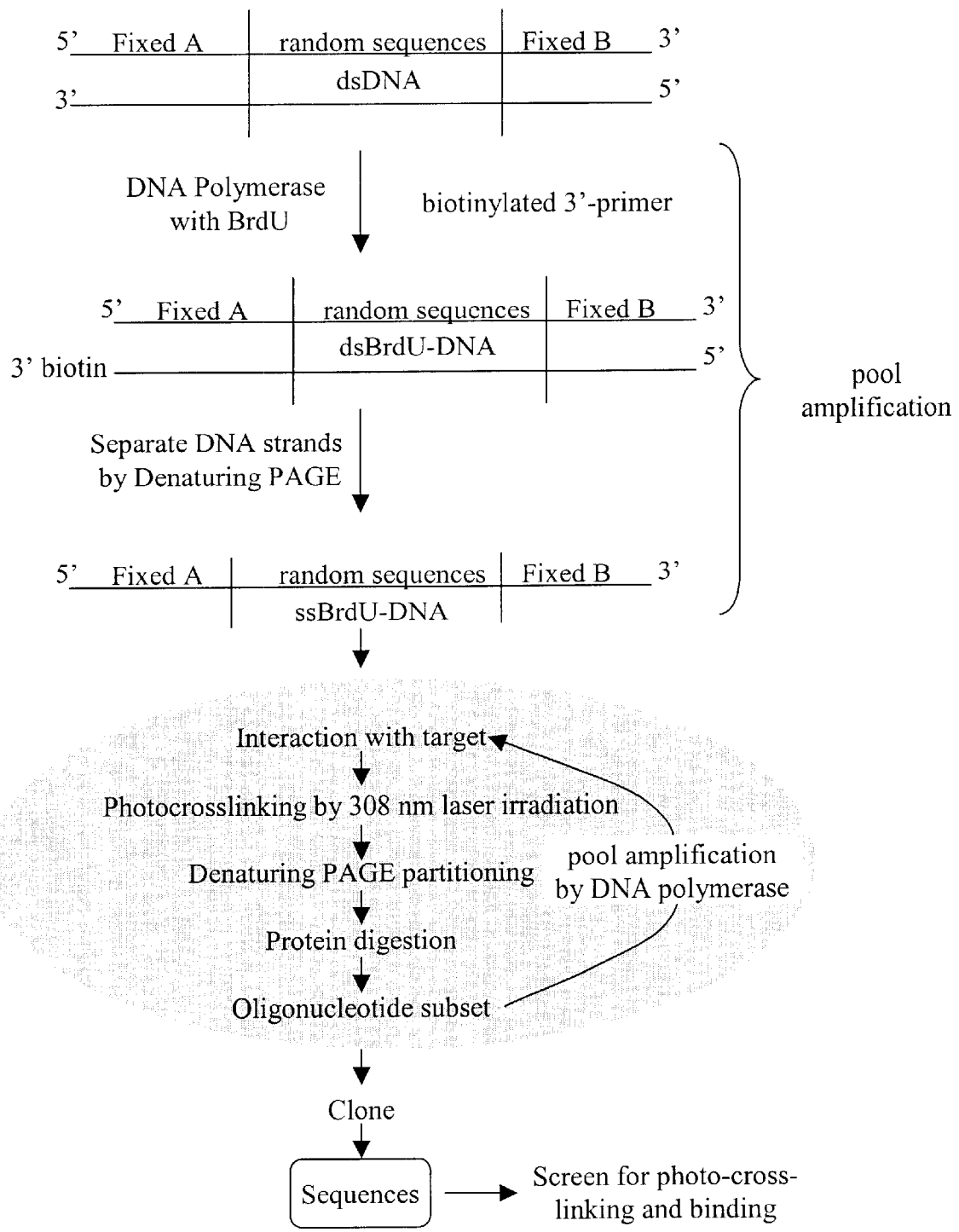
FIG. 1 depicts a flow chart illustrating the steps of photoselection of high affinity, high yield photocrosslinking ssDNA aptamers to a target protein.

The present invention includes a variation of the SELEX method for selecting nucleic acid ligands. This application hereby specifically incorporates by reference the full text including the definitions provided in the earlier SELEX patent applications, specifically those provided in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. application Ser. No. 09/459,553, filed Dec. 13, 1999, U.S. Pat. Nos. 6,001,577 and 5,763,177, each entitled "Systematic Evolution of Ligands by Exponential Enrichment: Photoselection of Nucleic Ligands and Solution SELEX," and U.S. patent application Ser. No. 08/123,935, filed Sep. 17, 1993, entitled "Photoselection of Nucleic Acid Ligands," now abandoned. The method of one embodiment of the present invention, termed photoSELEX, identifies and selects nucleic acid ligands capable of binding and/or photocrosslinking to target molecules.

Certain terms used to described the invention herein are defined as follows:

"Nucleic Acid Ligand" as used herein is a non-naturally occurring nucleic acid having a desirable action on a target. A nucleic acid ligand is also referred to as an "aptamer" herein. A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Photoaptamers" as used herein are nucleic acid ligands that contain a photoreactive group that can crosslink with the target. Photoaptamers can be generated in the following two ways: 1) by selecting aptamers for binding activity to a given target, modifying individual aptamers with a photoactive residue and screening for photocrosslinking activity; or 2) by incorporating photoactive residues into the SELEX library and selecting for photocrosslinking activity directly. Both methods work, however direct selection, which is referred to as PhotoSELEX is preferred, because it is more direct and appears to yield more-active photoapatmers. An ideal photoaptamer will react rapidly and in high yield with its target protein and will display little cross-reaction with non-target proteins.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to $bFGF_{(155)}$. The SELEX methodology is described in the SELEX Patent Applications, which are incorporated herein by reference in their entirety.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is $bFGF_{(155)}$.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the potential of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–10%) is retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

In the photoSELEX variation of SELEX, a modified nucleotide activated by the absorption of light is incorporated in place of a native base in either RNA or in ssDNA and the nucleic acid target molecule mixture is irradiated causing some nucleic acids incorporated in nucleic acid-target molecule complexes to crosslink to the target molecule via the photoreactive functional groups.

Partitioning means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Liquid-liquid partitioning can be used as well as filtration gel retardation, and density gradient centrifugation.

The nucleic acid ligands and nucleic acid ligand solutions to bFGF described herein are useful as diagnostic reagents. Further, the nucleic acid ligands to bFGF described herein may be used beneficially for therapeutic purposes.

The present invention also includes a method for determining the position of the nucleic acid ligand—target crosslink. In this variation of the present invention the photocrosslinked amino acid is identified by sequencing the photo-crosslinked amino acid nucleic acid ligand complex using Mass Spectrometry and the photo-crosslinked base is identified by Maxam-Gilbert sequencing.

Identification of ssDNA Ligands to $bFGF_{(155)}$ via PhotoSELEX

Figures 2A, 2B:
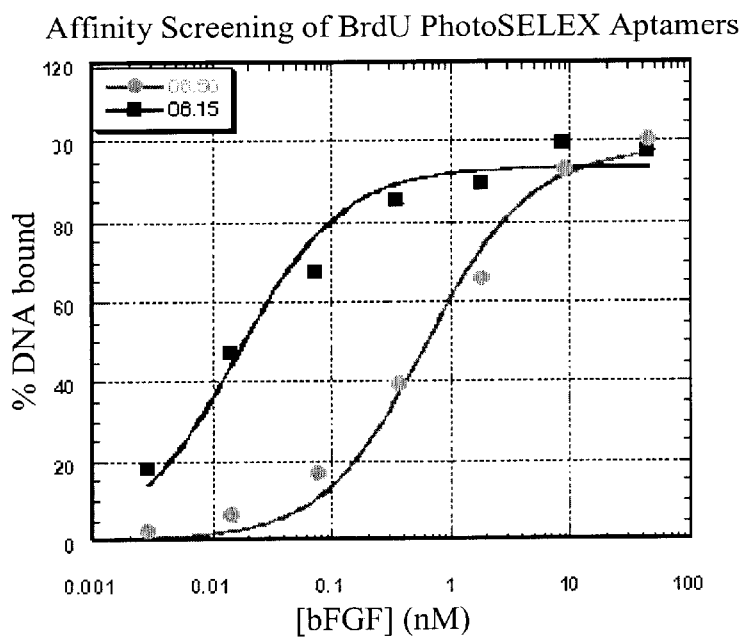
FIG. 2A depicts the sequences for PhotoSELEX-evolved BrdU aptamers identified as ligand 06.15 (SEQ ID NO:76) and ligand 06.50 (SEQ ID NO:70) for bFGF$_{(155)}$ (T=BrdU). The random region of the ligands is shown in upper case letters and the fixed regions appear in lower case lettering.
FIG. 2B depicts the binding affinity of ligands 06.15 and 06.50 for bFGF$_{(155)}$ as determined by nitrocellulose filter binding. $K_d$=16 and 560 pM for ligands 06.15 and 06.50, respectively.

A photoSELEX experiment employing a random 61-mer oligonucleotide library in which 5-bromo-2'-deoxyuridine replaced thymidine was completed against the $bFGF_{(155)}$ target as described in Example 1. The method is outlined in FIG. 1. Selection is based on the ability of unique ligands possessing the 5-bromouracil chromophore to form a photo-induced covalent bond to an aromatic or sulfur-bearing amino acid residue of the protein target. This was accomplished by irradiating the modified oligonucleotide library in the presence of the protein. Ligands which crosslink to the target were partitioned from those which did not by PAGE. The protein component of the nucleic acid/protein adduct was subsequently digested to generate sequences which could be amplified by PCR. Digestion removed most, but not all, of the attached protein because of the structure of the photocrosslinks (Dietz and Koch (1989) Photochem. Photobiol. 49:121–9; Dietz et al. (1987) J. Am. Chem. Soc. 109:1793–1797). The best amplification of these sequences used a combination of Taq and Pwo polymerase enzymes. Convergence to high affinity binding/high photocrosslink yielding ligands was achieved through six rounds of selection with simultaneous restriction of both target protein concentration and incident photons. Ligands were characterized by cloning and sequencing and upon measurement of binding and photocrosslinking yield, two ligands (06.15 (SEQ ID NO:76) and 06.50 (SEQ ID NO:70); FIG. 2A) were selected for further evaluation in a diagnostic assay.

This invention includes the specific DNA ligands to $bFGF_{(155)}$ shown in Tables 1 and 2 (SEQ ID NOS:4–98), identified by the methods described in Example 1. The scope of the ligands covered by this invention extends to all nucleic acid ligands of $bFGF_{(155)}$, modified and unmodified, identified according to the SELEX procedure. More specifically, this invention includes nucleic acid sequences that are substantially homologous to the ligands shown in Tables 1 and 2 and FIG. 2A (SEQ ID NOS:4–98). By substantially homologous it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of bFGF$_{(155)}$ shown in Tables 1 and 2 and FIG. 2A (SEQ ID NOS:4–98) shows that some sequences with little or no primary homology may have substantially the same ability to bind bFGF$_{(155)}$. For this reason, this invention also includes nucleic acid ligands that have substantially the same structure and ability to bind bFGF$_{(155)}$ as the nucleic acid ligands shown in Tables 1 and 2 and FIG. 2A (SEQ ID NOS:4–98). Substantially the same ability to bind bFGF$_{(155)}$ means that the affinity is within one or two orders of magnitude of the affinity of the ligands described herein. It is well within the skill of those of ordinary skill in the art to determine whether a given sequence—substantially homologous to those specifically described herein—has substantially the same ability to bind bFGF$_{(155)}$.

Upon mixing with a target protein, the photoaptamer forms a stable, reversible Michaelian complex [A:T] with dissociation constant K$_D$. The existence of this complex is supported by nitrocellulose filter-binding affinity measurements. The requirement of this complex for crosslinking is shown by the elimination of crosslinking under denaturing conditions. This complex can absorb a photon and form an irreversibly crosslinked complex (A×T) with the first-order rate constant k$_{xl}$. In addition, some photoinactivation of the aptamer is also observed. The rate of inactivation is not strongly affected by the presence of the protein.

Ligand Sensitivity

Ligands 06.50 (SEQ ID NO:70) and 06.15 (SEQ ID NO:76)) identified via the photoSELEX methodology are set forth in FIG. 2A. The method used to evaluate the sensitivity of these two ligands to bFGF is described in Example 2. Although an extensive investigation of the various characteristics of these ligands, such as, their tertiary structures was not undertaken, one property salient to their potential as diagnostics which was determined is the yield with which they form a photocrosslinked adduct with the target protein. In one embodiment, the higher the crosslink yield, the greater the potential for detection of the target. As described more fully below in Example 2, the crosslink yield was measured by combining a quantified activity of each 5'-$^{32}$P-radiolabeled ligand (≈1–5 fmol) with an excess of bFGF$_{(155)}$ (≈5 pmol) diluted in 1×phosphate buffered saline (PBS) to 25 nM. These ligand/protein mixtures were then irradiated with a XeCl excimer laser and the result analyzed by sodium dodecyl sulfate polyacrylamide gel electrophoresis (SDS-PAGE) partitioning. Phosphorimage analysis revealed that ligand 06.50 (SEQ ID NO:70) gave a crosslink yield of 81% while ligand 06.15 gave a crosslink yield of 50%. Measurement of the quantum yield of photocrosslinking is difficult in such dilute macromolecular systems. However, the observed yield for the photon dose suggests that both ligand 06.50 and ligand 06.15 crosslink bFGF$_{(155)}$ efficiently relative to a well established bromouracil nucleoprotein photocrosslinking reaction (Gott et aL (1991) Biochemistry 30:6290–6295). No other nucleoprotein system incorporating 5-bromodeoxyuridine has been reported with a photocrosslinking yield as high as that described here for ligand 06.50/bFGF$_{(155)}$ (Meisenheimer and Koch (1997) Crit. Rev. Biochem. Mol. Biol. 32:101–140).

Target molecule sensitivity was also assessed for these ligands by determining their binding affinity through nitrocellulose filter binding. As can be seen in FIG. 2B, both ligands exhibit impressive binding affinities for bFGF$_{(155)}$ with 06.15 achieving an unusually strong association (K$_d$≈16 pM for 06.15 and ≈560 pM for 06.50). While it is clear that the detection limit of the immunoassay depends primarily on the binding affinity of a monoclonal antibody for an antigen, the formation of an affinity-based nucleoprotein complex is also a crucial precursor to a photocovalent adduct. This is a simple consequence of the photoreactive nucleotide and amino acid residue being held in a conformation suitable for electron transfer and subsequent covalent bond formation. (Meisenheimer and Koch (1997) Crit. Rev. Biochem. Mol. Biol. 32:101–140; Norris et al. (1996) J. Am. Chem. Soc. 118:5796–5803). It is interesting and perhaps paradoxical that the relative quantum yield of crosslinking, as estimated from the crosslinking yield, and the binding affinity are not in concert for these ligands even though both are important to analyte detection. Despite this incongruity, both exhibited good potential as diagnostic agents which prompted a quantitative assessment of their ability to detect bFGF$_{(155)}$.

Figure 3A:
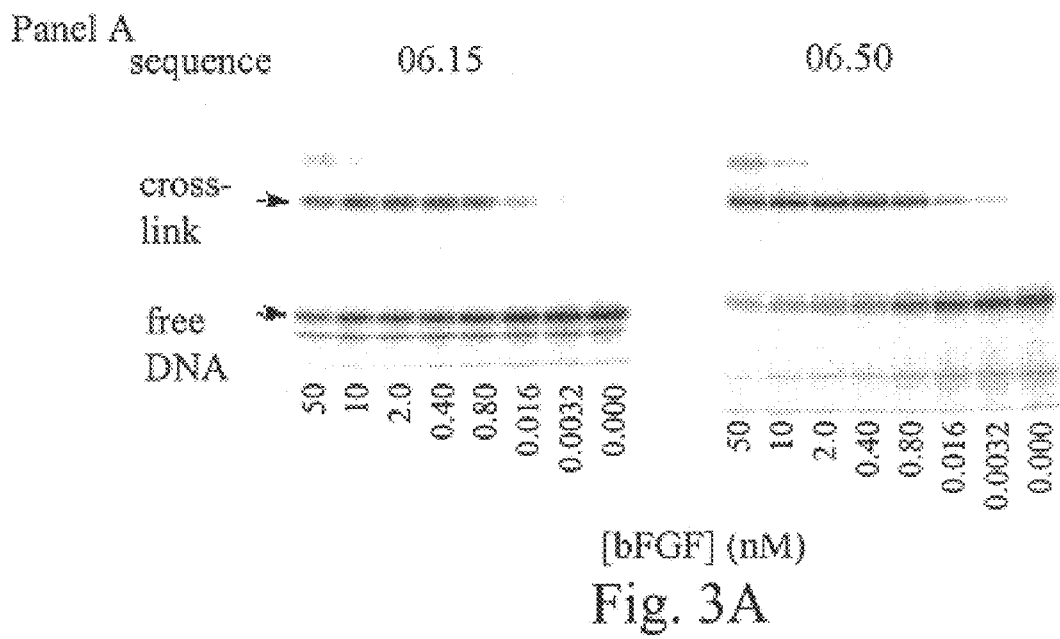
FIG. 3A illustrates the sensitivity of ligands 06.15 and 06.50 for bFGF$_{(155)}$ as assessed by 12% SDS-PAGE analysis of photocrosslinked adduct formed in phosphate buffered saline.

An absolute assessment of target molecule sensitivity was made by performing a photocrosslinking analog to the thermal binding curve. Various concentrations of bFGF$_{(155)}$ were prepared by serial dilution with 1×PBS (just as when performing a standard nitrocellulose filter binding measurement). To each concentration of bFGF$_{(155)}$ (including a sample with no bFGF$_{(155)}$) a quantified activity of 5'-$^{32}$P-radiolabeled ligand was added. However, rather than measuring signal as sequestered by nitrocellulose filter binding, the ligand/protein mixtures were irradiated with a XeCl excimer laser. The result of each reaction was analyzed by SDS-PAGE which partitioned uncrosslinked 5'-radiolabeled ligand from ligand photocrosslinked to bFGF$_{(155)}$. Since the limit of detection is the lowest bFGF$_{(155)}$ concentration that yields a crosslink signal, this experiment provided a measure of the sensitivity limit of ligands 06.15 and 06.50 for bFGF$_{(155)}$ as the ligands might be employed in the kind of diagnostic system discussed below. The results of this experiment are shown in FIG. 3A.

For each ligand, a crosslink signal can be observed at bFGF$_{(155)}$ concentrations as low as 0.0032 nM using a total activity of 20,000 cpm in each lane and 0.5 h phosphorimage exposure. This is exceptional sensitivity for a non-amplified technology and corresponds to a detection capability of 58 pg/mL or 0.058 ppt of bFGF$_{(155)}$. Confidence in this result is enhanced by a distinct crosslink signal difference between 0.0032 nM and 0.000 nM bFGF$_{(155)}$. Presumably, even lower concentrations could be detected in this way by increasing the total activity of radiolabeled ligand and phosphorimage exposure time.

The observation that ligand 06.15 exhibited substantially better affinity binding for bFGF$_{(155)}$ than did ligand 06.50, but showed approximately the same crosslink signal at 0.0032 nM bFGF$_{(155)}$ may at first seem counterintuitive. In fact, the crosslink signal at 0.0032 nM bFGF$_{(155)}$ is slightly greater for ligand 06.50 than for 06.15. Evidently, ligand 06.50's superior crosslinking efficiency more than compensated for its lower binding affinity. Nevertheless, both ligand 06.15 and ligand 06.50 exhibited impressive sensitivity to bFGF$_{(155)}$ as measured by SDS-PAGE analysis of the crosslink signal. Another important diagnostic property to assess for these ligands was their specificity for bFGF$_{(155)}$.

Ligand Specificity

Figure 3B:
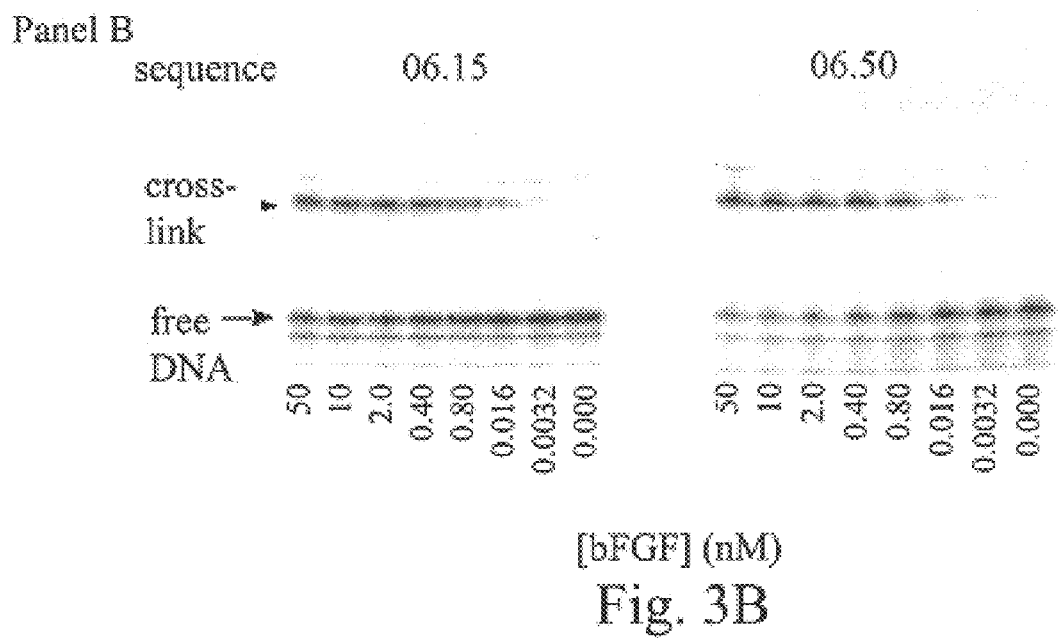
FIG. 3B illustrates the specificity of ligands 06.15 and 06.50 for bFGF$_{(155)}$ as assessed by 12% SDS-PAGE analysis of photocrosslinked adduct formed in 10% serum/90% phosphate buffered saline. In all four gels the crosslink band is still observable at 0.0032 nM bFGF$_{(155)}$ with both ligands and no crosslink band is observed in the absence of bFGF$_{(155)}$.

The specificity of ligands 06. 15 and 06.50 for bFGF$_{(155)}$ was established in three experiments. First, the binding affinity of these ligands was determined for three other members of the heparin-binding family of proteins: Vascular Endothelial Growth Factor (VEGF), Platelet Derived Growth Factor (PDGF) and thrombin. Binding affinity was measured by nitrocellulose filter binding as described above, with the normalized results which gave K$_d$ values for VEGF, PDGF and thrombin greater than three orders of magnitude larger than the K$_d$ values of ligands 06.15 and 06.50. Hence, both ligands 06.15 and 06.50 readily distinguish between proteins based on affinity binding. The normalized results are set forth in Table 3. Second, the crosslink signal for ligands 06.15 and 06.50 with bFGF$_{(155)}$ was again measured via SDS-PAGE, but this time in the presence of 10% serum as the crosslinking medium as described in Example 3. Since serum contains an immense array of proteins, nucleic acid and heparin binding proteins are likely present. Therefore, any crosslink signal in the absence of bFGF$_{(155)}$ may indicate a concern regarding the crosslinking specificity of these ligands. As can be seen in FIG. 3B, neither ligand 06.15 nor 06.50 yield any crosslink signal at the position of the bFGF$_{(155)}$ crosslinking band in the absence of bFGF$_{(155)}$. Third, the crosslink yield was measured for ligands 06.15 and 06.50 via SDS-PAGE with both VEGF and PDGF. Even at 25 nM protein concentrations, neither ligand showed any identifiable photocovalent adduct in either PBS or 10% serum crosslinking environments (data not shown).

These experiments serve to illustrate the feasibility of using photoligands in a diagnostic system. In particular, since identification of protein markers or specific antigens from a patient will likely be made from a serum or plasma extract, the observation that the absolute sensitivity of these ligands is not reduced in a 10% serum crosslinking environment is encouraging. It should be noted, however, that the slightly greater crosslink signal at low bFGF$_{(155)}$ concentration exhibited by ligand 06.50 in the PBS environment was lost in the 10% serum environment. Careful examination shows that the crosslink signal for ligand 06.50 is nearly halved in the 10% serum environment for 0.0032 nM bFGF$_{(155)}$ compared to the signal detected for 0.0032 nM bFGF$_{(155)}$ in the PBS environment. Conversely, virtually no change in crosslink yield was observed for ligand 06.15 under the same conditions. Presumably, non-specific binding of proteins in serum partially inhibited binding by ligand 06.50 and correspondingly, lowered the crosslink yield. Here, then, is strong evidence in support of the importance of target affinity for photoSELEX-evolved diagnostics. These results indicate the feasibility of photoSELEX-evolved diagnostics, but they also indicate the importance of identifying the very best photocrosslinking ligands for use in diagnostic systems.

A Diagnostic System

Figure 4:
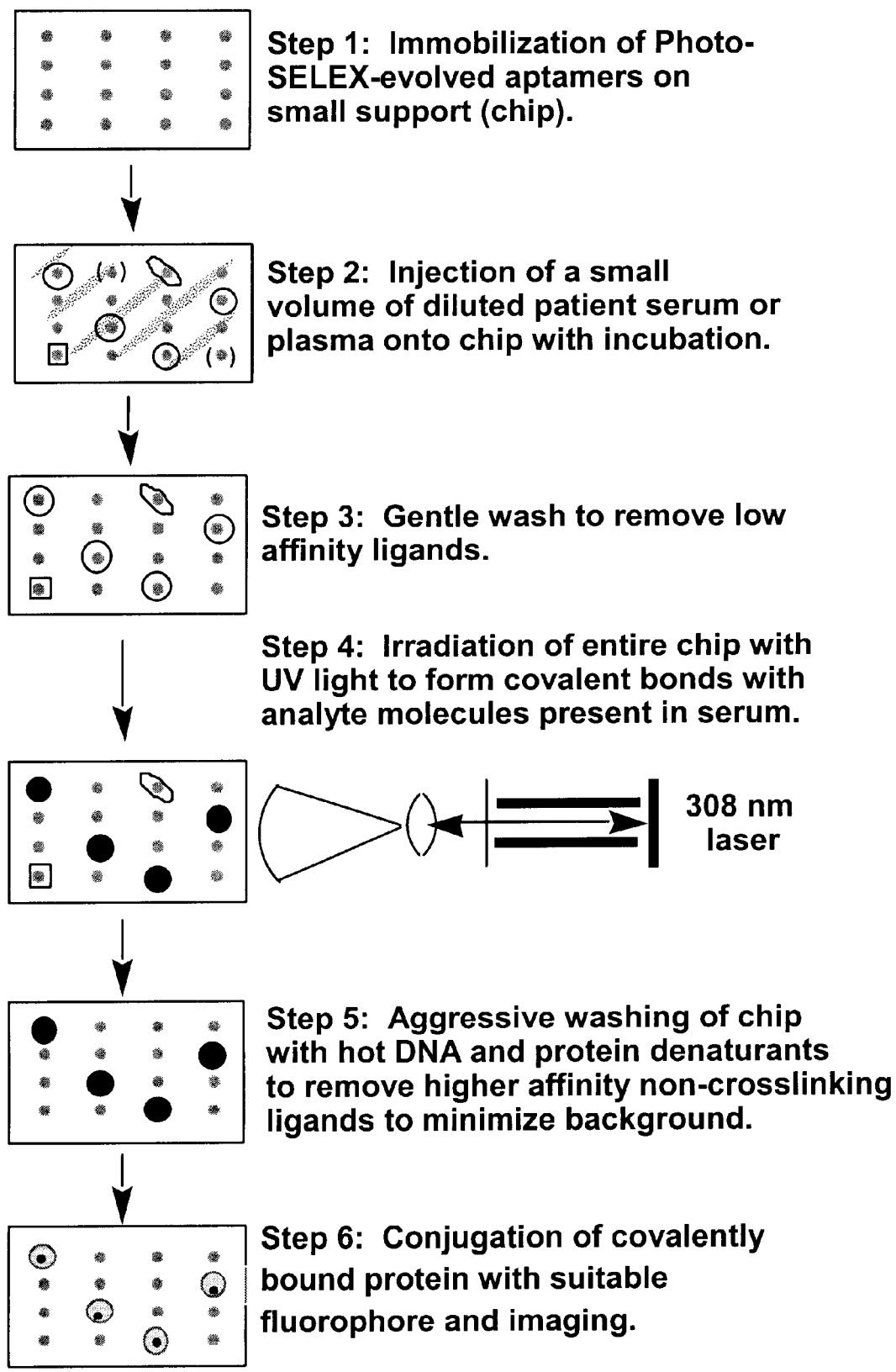
FIG. 4 illustrates the PhotoSELEX fluorescent assay concept.

Both ligand 06.15 and ligand 06.50 demonstrate solid potential for photoSELEX-evolved diagnostics. Use of aptamers on a solid support is described in U.S. patent application Ser. 09/561,465, filed Jun. 12, 2000 and U.S patent application Ser. No. 08/990,436, filed Jun. 15, 1997, both entitled "Nucleic Acid Ligand Diagnostic Biochip," each of which is incorporated herein by reference in its entirety. A design of a practical diagnostic replacement to current immunoassay systems, referred to as the photoSELEX diagnostic system, using this method is illustrated in FIG. 4. With reference to FIG. 4, photoSELEX-evolved ligands are generated for many different marker proteins. Once evolved, these ligands are immobilized on a solid surface somewhat like the capture antibody of the ELISA sandwich technique. However, rather than immobilizing just one type of ligand somewhat randomly within a well of a microtitre plate, the various photoSELEX-evolved ligands are fixed on a very small solid support in a specific pattern such as in a grid. The ability to deposit DNA precisely on a solid support has been demonstrated and used to identify active genes in fibroblasts in response to serum introduction (Iyer et al. (1999) Science 283:83–87).

With the ligands bonded to the solid support (chip), a suitably prepared patient sample is applied to the chip with each ligand forming an affinity association with its target molecule. After appropriate incubation, the solid support is gently washed to remove low affinity proteins before irradiation as shown in FIG. 4. This step removes the majority of protein material which might form a non-specific photocrosslink. An example of low level non-specific photocrosslinking is evident in FIG. 3B which shows a faint band just above the specific photocrosslink band. This band is dependent upon the presence of serum, but independent of bFGF concentration suggesting that it results from photocrosslinking to a BrdU remote from the specific photocrosslinking BrdU. As indicated in FIG. 2, ligand 06.15 has five BrdUs and ligand 06.50 has seven. The chip is then irradiated with UV light causing covalent bond formation between ligand and target. For both ligand 06.15 and 06.50, the covalent bond formed between a specific BrdU in the ligand sequence and Tyr 133 of bFGF$_{(155)}$ was observed to be so robust as to permit its identification by electrospray mass spectrometry. (Golden et al. (1999) Protein Sci. 8 2806–2812). As a result, very aggressive washing of the plate after irradiation with hot detergents and denaturants is used to eliminate the remainder of nonspecific associations with a significant decrease in background signal. Finally, the solid support is exposed to a universal fluorescent dye capable of conjugating specific amino acids of the covalently bonded proteins, and the chip is quantitatively evaluated. Any other detection method, such as surface plasmon resonance (SPR), is also contemplated.

In the photoSELEX-based diagnostic system, hundreds or thousands of analyte molecules could be quantified with a single sample of patient serum. This contrasts with the ELISA sandwich immunoassay system which is currently used to test for a single analyte molecule from numerous patients at a time. With this design, a photoSELEX-based diagnostic system has potential for high throughput quantification of multiple proteins with impressive specificity using minimal sample. Other factors in favor of the photoSELEX-based technology are potential long chip shelf-life, ease of automation, and a totally in vitro technology.

Determination of the bFGF Crosslinking Amino Acid

An important aspect in the characterization of any oligonucleotide/protein crosslink system is the identification of a protein's crosslinking amino acid. In many cases the primary motivation for forming the photocovalent crosslink bond is to identify the point of contact between the oligonucleotide and the protein. While several techniques have been developed to locate the crosslinking amino acid, the primary method used to date is Edman degradation of the protein after formation of the covalent bond. Using this method, a given protein is sequenced starting at the amino terminus with phenylisothiocyanate and trifluoroacetic acid through to the carboxy terminus. Following treatment with aqueous acid, each phenylthiohydantoin-amino acid is detected chromatographically by high performance liquid chromatography (HPLC). This sequence is then compared to the protein's known sequence. The amino acid which fails to be detected corresponds to the crosslinking amino acid. In practice, Edman degradation protein sequencing is limited to 40 to 60-N-terminal residues as a result of side reactions, incomplete reactions and peptide loss. Also, since as little as one picomole of any individual amino acid may be chromatographically detected, Edman degradation may reliably sequence approximately 10 pmol of a 40-mer peptide. Edman degradation of ligands 06.50 and 06.15 is described in Example 4.

With reference to the primary amino acid sequence for bFGF set forth in the Background of the Invention, it can be seen that the photocrosslinking amino acid, as determined by Edman degradation is the tyrosine at position 133 of the amino acid sequence (Tyr133). This result substantiates a fundamental premise of SELEX in general and photo-SELEX in particular—that the photochemical pressure has identified the most facile photocrosslinking amino acid. It is known that the aromatic amino acids including histidine, tryptophan, phenylalanine and tyrosine possess the greatest ability of all the amino acids to crosslink with BrdU. This is a result of the relatively low ionization potential of these residues. Tyrosine has been shown to be the most photoactive amino acid available.

Figure 6:
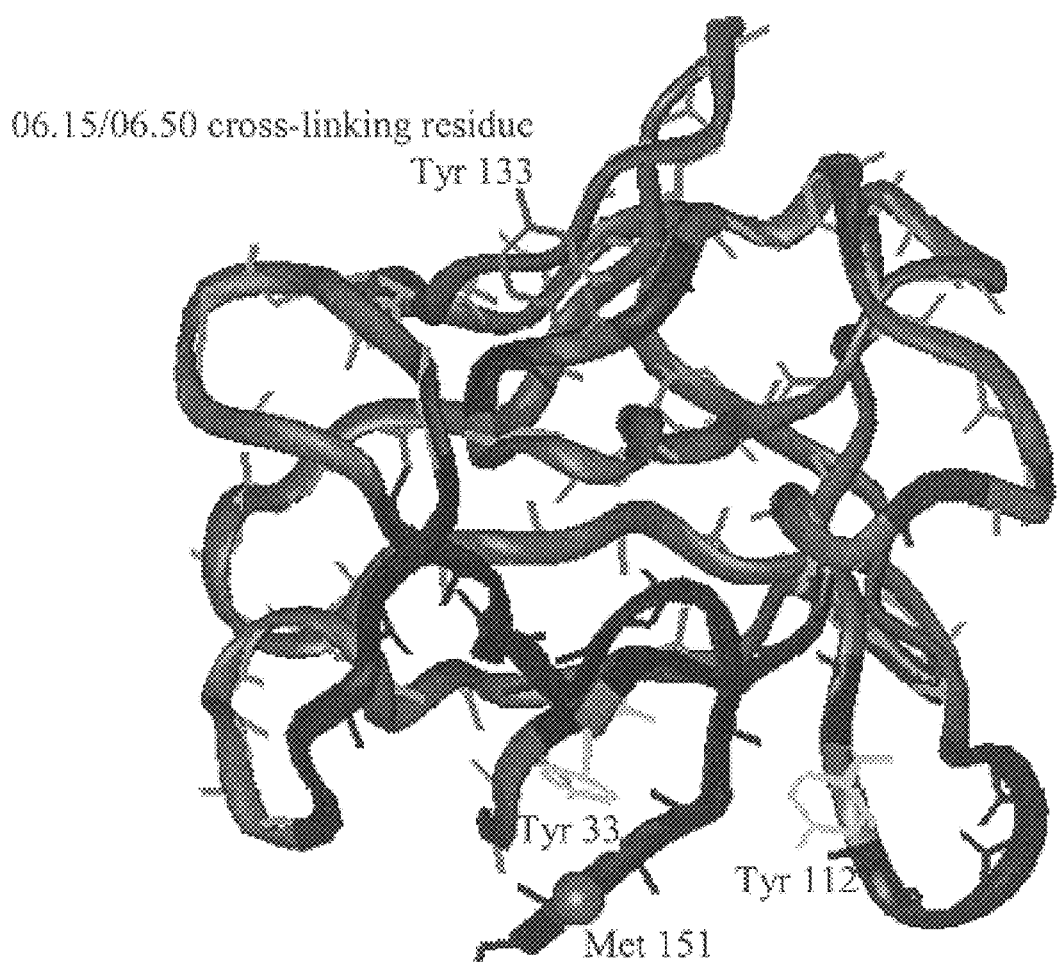
FIG. 6 illustrates bFGF$_{(155)}$ ribbon structure showing Tyr133, the crosslinking amino acid.

Additionally, photoSELEX has identified ligands which bind to the most critical region of bFGF's heparin-binding epitope. Although ligands 06.15 and 06.50 do not seem to share any apparent sequence homology, they both crosslink to Tyr133 of bFGF$_{(155)}$ whose position in the peptide is shown in FIG. 6. Moy et al. (1996) Biochemistry 35:13552–13561, have identified a helix-like conformation within the known heparin-binding epitope of bFGF which they surmise may play a crucial role in heparin recognition. It is particularly interesting to note that as this helix includes residues 131–136 and photoSELEX has evolved ligands which covalently bind at the heart of the heparin binding site. Eriksson et al. (1993) Protein Sci. 2:1274–1284, also contend that substantial evidence implicates Lys125(134) as the key to heparin binding. While these results are very positive in themselves, the ability of photoSELEX to identify such high quantum yield crosslinking ligands for a protein target presented an opportunity to explore the ability of mass spectrometry to sequence and identify peptides with post-translational modifications.

Over the past 30 years mass spectrometry has emerged as an exceptionally useful tool in macromolecular characterization. The ability of mass spectrometry to sequence simple peptides was first demonstrated in the early 1970s (McLafferty et al. (1973a) J. Am. Chem Soc. 95:2120; McLafferty et al. (1973b) J. Am. Chem. Soc. 95:3886). Somewhat more recent advancements in mass spectrometric methods have permitted sequencing of polypeptides providing an attractive alternative to Edman degradation, which cannot sequence peptides with post-translational modifications (e.g., blocked N-termini and glycosylated, phosphorylated or acetylated residues). In particular, fast atom bombardment (FAB) with tandem mass spectrometry (MS-MS) has evolved as a successful mass spectrometric method for polypeptide sequencing. In this technique, the polypeptide is first dissolved in a solvent of low volatility, such as glycerol, and subsequently bombarded with a beam of argon or xenon atoms. Bombardment of glycerol/peptide solution yields (M+H)$^+$ ions which can be detected and selected with the first mass spectrometer from other peptides or unwanted contaminants which may be present. The selected ion can then be fragmented by He atoms (or other inert atoms) and analyzed by the second mass spectrometer. The key to the success of FAB/MS-MS (as well as more advanced mass spectrometric methods used in this research) is that the polypeptide will fragment in known ways from both the N and C-termini to yield fragmentation patterns which can be deciphered as an unique amino acid sequence.

Roepstoff and Fohlman (1984) Biomed. Mass Sectrom. 11:601 with subsequent modification by Biemann (1988) Mass Spectrom. 16:99 established the nomenclature currently used for peptide fragmentation ions. The assignment of a peptide fragment ion is based upon whether the fragment results from amide-backbone bond or residue side chain bond cleavage and whether charge retention occurs with either the N-terminal or C-terminal amino acid fragment. The amino acid fragment ions which can be generated in MS from backbone bond cleavage and the associated nomenclature are illustrated below. Although FAB/MS-MS readily generates fragment ions resulting from side chain bond cleavage, more advanced techniques employed in this research generate backbone bond cleavage almost exclusively.

FAB/MS-MS has two particular advantages over Edman degradation. First, as mentioned above, mass spectrometry can sequence peptides with post-translational modifications. Second, mass spectrometric peptide sequencing can be completely automated and computerized making the process much faster than Edman degradation. The significant disadvantage associated with FAB/MS-MS is reduced sensitivity. Since it is difficult and expensive to produce nanomolar quantities of trypsin digested crosslinked nucleoprotein adduct, reduced sensitivity is a substantial drawback to any sequencing methodology. Fortunately, more recent advances in mass spectrometric techniques have significantly enhanced sensitivity.

Electrospray mass spectrometry has recently emerged as a very effective method for sequencing peptides with post-translational modifications. In this technique, an organic/aqueous solvent mixture (including the analyte) is injected into a high potential field through a very small gauge needle. This atomization generates charged droplets which are accelerated toward the instrument's analyzer. This acceleration phase takes place in a vacuum which promotes evaporation of the droplet's solvent. Evaporation yields smaller, less stable charged droplets from which molecular ions are subsequently emitted. Finally, these ions are focused and accelerated by quadropole analyzers which separate the ions according to m/z. Electrospray mass spectrometry (ESMS) is unique in that it does not require fragmentation to generate ions. As a result, substantially more molecular ions are generated for a given sample with concomitant enhancement in sensitivity. Finally, the m/z ions of interest can be selected and fragmented by the MS-MS method as described above for FAB/MS-MS. Thus, ESMS utilizes the inherent advantages of FAB/MS-MS while eliminating its lack of sensitivity.

Advanced mass spectral techniques have been successfully employed to characterize certain aspects of covalently bound oligonucleotide/protein adducts. For instance, several research groups have shown that the matrix assisted laser desorption ionization (MALDI) and HPLC/electrospray ionization (ESI) MS can be used to establish the molecular mass of proteins crosslinked to oligonucleotides (Jensen et al. (1993) Rapid Commun. Mass Sprectrom. 7:496–501; Bennett et al. (1994) J. Biol. Chem 269:21870–21879; Jensen et al. (1995) J. Mol. Biol. 235:237–247; Connor et al. (1998b) Photochem. Photobiol. 68:299–308; Wong et al. (1998) Nucleic Acids Research 26:645–649). In addition, sequencing by collision-induced dissociation (CID) of model peptides crosslinked to a homogeneous oligonucleotide T$_6$ and of peptides cross-linked to mono or dinucleotides has been characterized with MALDI mass spectrometry coupled with N-terminal microsequencing and alkaline RNA hydrolysis (Urlaub et al. (1997) J. Biol. Chem 272:14547–14555). Although these cases show the potential for a mass spectral characterization of protein-nucleic acid crosslinks, MS sequencing of a crosslinked high affinity protein-nucleic acid complex by CID has not been previously reported.

Example 5 illustrates a method for the determination of the bFGF crosslinking amino acid using mass spectrometry. The results of this experiment, which are set forth in FIGS.

7–10 and Table 4, confirm Tyr133 as bFGF's crosslinking amino acid to the 06.50 ligand. The polypeptide fragmentation nomenclature used in Table 4 was established by Roepstoff and Fohlman (1984) Biomed. Mass Sectrom. 11:601 with subsequent modification by Biemann (1988) Mass Spectrom. 16:99. The assignment of a peptide fragment ion is based upon whether the fragment results from amide-backbone bond or residue side chain bond cleavage and whether charge retention occurs with either the N-terminal or C-terminal amino acid fragment. The amino acid fragment ions which can be generated in MS from backbone bond cleavage and the associated nomenclature are illustrated below. Although FAB/MS-MS readily generates fragment ions resulting from side chain bond cleavage, more advanced techniques employed in this research generate backbone bond cleavage almost exclusively.

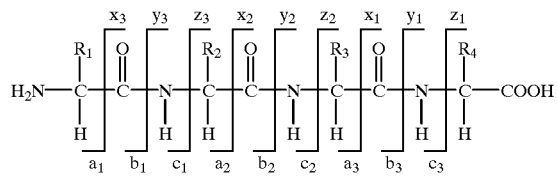

The facility of the ESMS/MS technique to rapidly sequence a small quantity of photocrosslinked oligonucleotide/protein adduct is an exciting first in peptide sequencing technology. These results reaffirm the usefulness of ESMS to sequence post translationally modified ligands. More importantly, they enhance the usefulness of photocrosslinking oligonucleotide/protein complexes as a tool of structure elucidation.

Determination of the Crosslinking Position on the Oligonucleotide

The final aspect to complete characterization of the covalently bound oligonucleotide/protein adduct is the determination of the crosslinking position on the oligonucleotide. This not only helps elucidate the oligonucleotide contact point and thereby important structural characteristics of the adduct, but it can also be useful in any post-SELEX modification (e.g., replacing a BrdU with IdU at the crosslinking position in an attempt to increase crosslink yield while retaining robust photochemistry). In the past, crosslinking positions have been determined by single substitution experiments.

It seemed possible to identify the crosslink position on the oligonucleotide if the protein could be substantially (but not completely) digested enzymatically followed by a systematic cleavage of the oligonucleotide itself. The Maxam-Gilbert sequencing technique provides just this kind of systematic cleavage. Maxam-Gilbert sequencing was invented by Allan Maxam and Walter Gilbert in 1980 to sequence DNA. (Maxam and Gilbert (1980) Methods Enzym. 65:499–650). Its objective is to chemically cleave 5'-$^{32}$P-labeled DNA in a base-specific manner, so that, on average, each DNA strand is randomly cleaved at only one susceptible position. This yields a series of DNA fragments which correspond in length to the position of a particular base from the 5' end. For instance, the Maxam-Gilbert sequencing of the oligonucleotide:

$^{32}$P-GAGCTTCAGGCCGTCAT-3 ' under conditions which specifically cleave at the 5' end of the cytidine nucleotides would result in the following DNA fragments:

$^{32}$P-GAGCTTCAGGCCGTCAT-3'

$^{32}$P-GAGCTTCAGGCCGT $^{32}$P-GAGCTTCAGGC $^{32}$P-GAGCTTCAGG $^{32}$P-GAGCTT $^{32}$P-GAG

Figure 12:
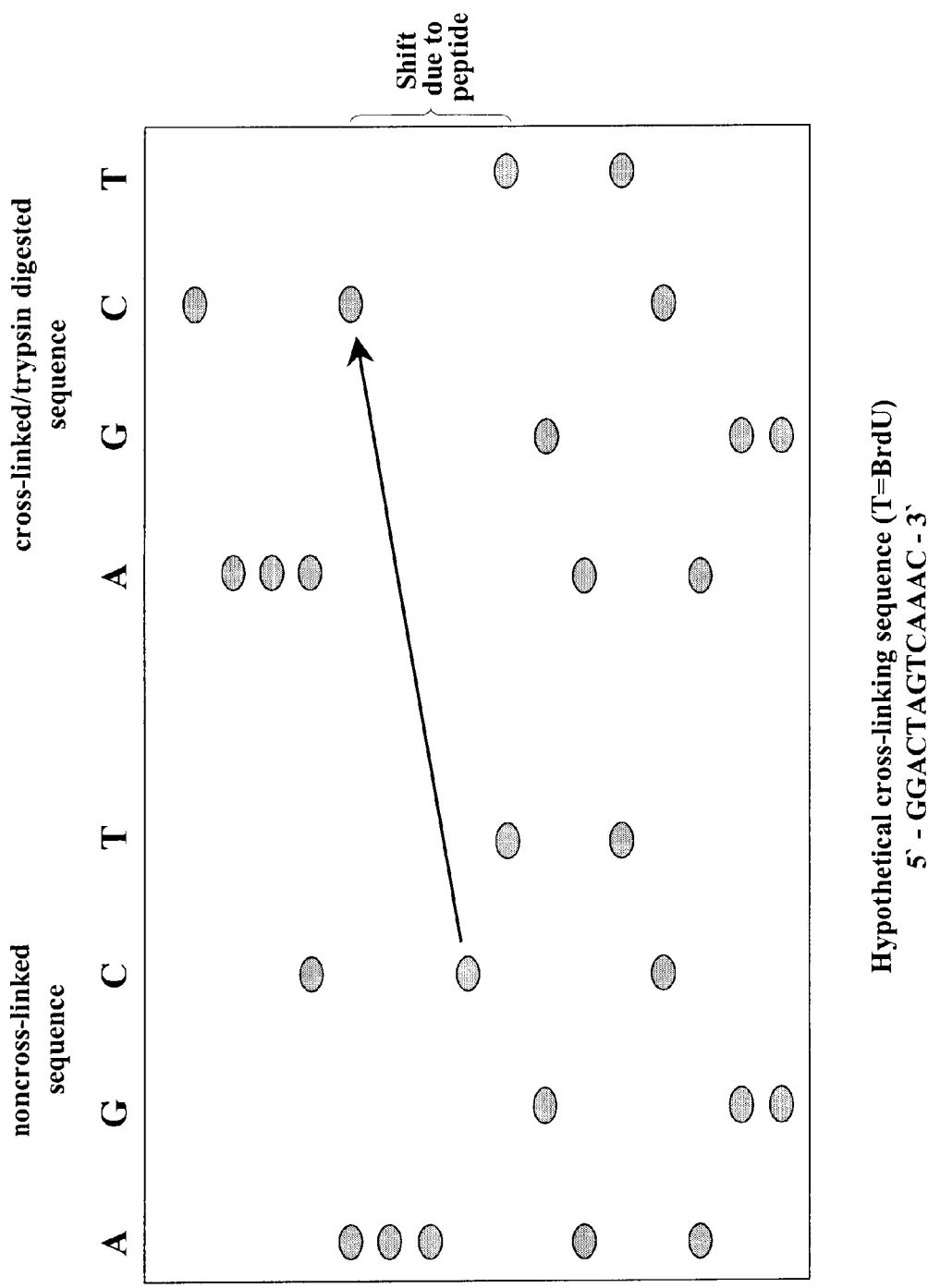
FIG. 12 depicts the Maxam-Gilbert sequencing determination of the crosslink position on a hypothetical photoSELEX-evolved ligand.

These fragments are are then separated by PAGE and the C-positions read directly from an autoradiogram. A full complement of such base-specific cleavage reactions permits determination of the entire oligonucleotide sequence. An oligonucleotide crosslinked to bFGF with subsequent digestion of a protein would be chemically cleaved in an identical manner. The only difference in appearance between the Maxam-Gilbert sequencing of the noncrosslinked and crosslinked versions of a given ligand would be a gel shift at the crosslinking base corresponding in magnitude to the size of the protein fragment. Since moderate, but significant shift, would permit ready identification of the crosslink position, it seemed a peptide fragment approximately ten amino acids long would be ideal. Conveniently, this is just about the peptide fragment remaining after trypsin digestion of the 06.50/bFGF crosslinked adduct. After the shift, the Maxam-Gilbert sequencing gel for the digested crosslinked adduct would again appear identical to the noncrosslinked version except all bands would be shifted up the gel a constant amount corresponding to the peptide fragment. FIG. 12 illustrates the conceptualized Maxam-Gilbert sequencing gel of both the noncrosslinked and crosslinked digested versions of a hypothetical crosslinking ligand (5'-GGACTAGTCAAAC-3' (SEQ ID NO:100).

Figure 13:
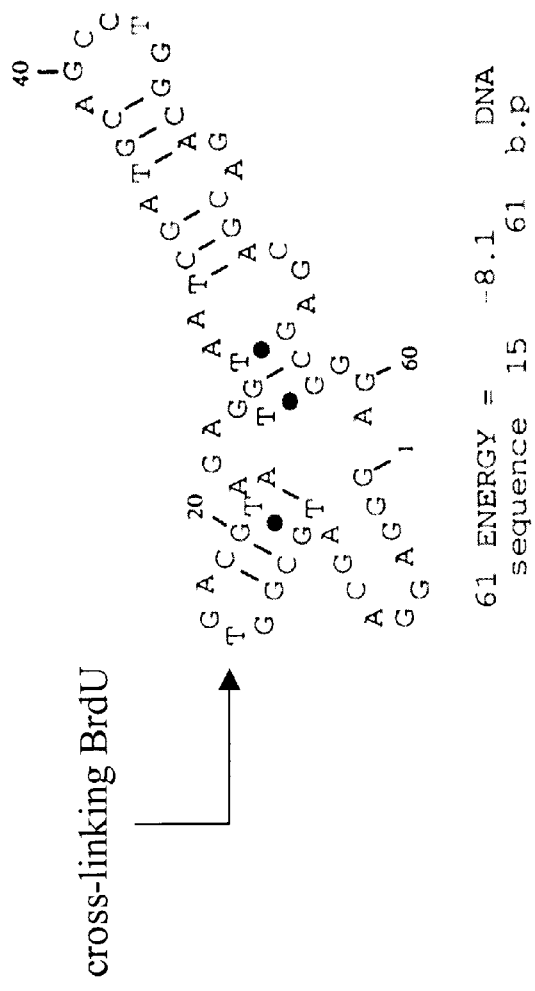
FIG. 13 illustrates the MulFold secondary structures for ligand 06.50.
Figure 13:
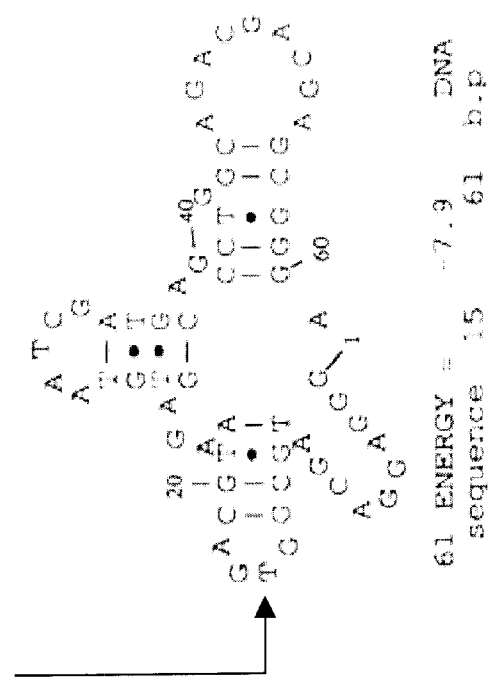

Finally, the identification of the crosslinking nucleotide in ligand 06.50 appears to corroborate the structures generated by the MulFold program. The base position was placed in protein-accessible hairpin loops for the two most stable secondary structures for ligand 06.50 which are shown FIG. 13.

Some key characteristics of a useful protein probe are that its activity—target crosslinking should be fast and high-yield; and its specificity—crosslinking should be to the target only. To carefully evaluate these characteristics first it was determined that the crosslinking reaction shows saturation kinetics with respect to both time and protein concentration, thus allowing quantification of activity as a second-order rate constant. Second, crosslinking specificity was evaluated by determining the rate constants for target vs non-target crosslinking. The non-target proteins were platelet-derived growth factor (PDGF), and thrombin, two heparin-binding proteins which might be expected to have substantial non-specific affinity for DNA photoaptamers. Third, specificity of crosslinking was compared to the specificity of affinity binding alone, to determine whether the crosslinking step enhances or degrades the specificity of the aptamer-target interaction.

Measurement of Crosslinking Rates

Figure 14:
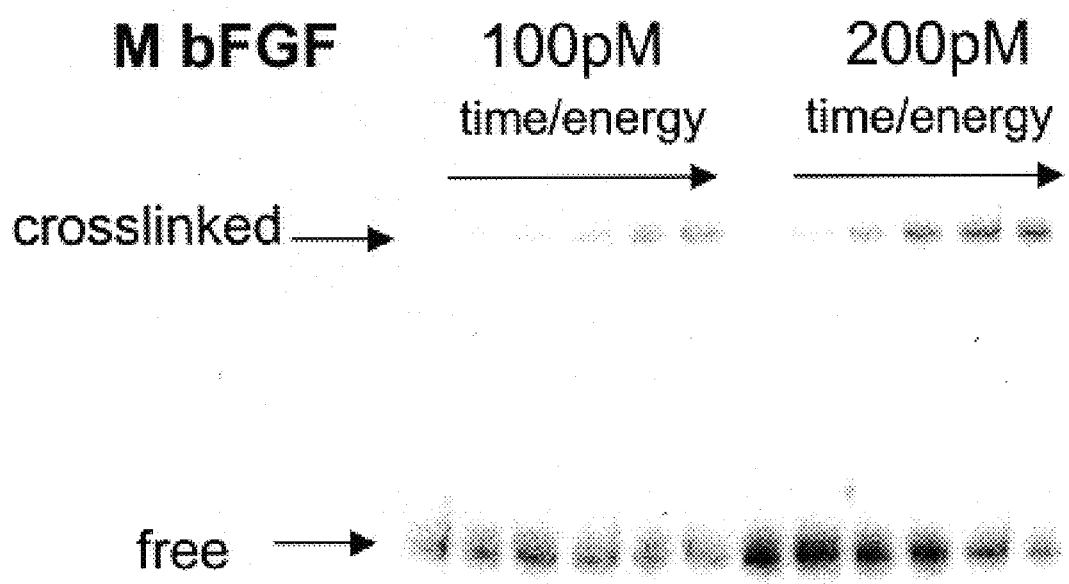
FIG. 14 depicts the increase in crosslinking as a function of irradiation and concentration. The sample was irradiated at 308 nm by a XeCl laser at 2 mJ/pulse, 200 Hz. Samples were analyzed by SDS/urea PAGE.
Figure 15:
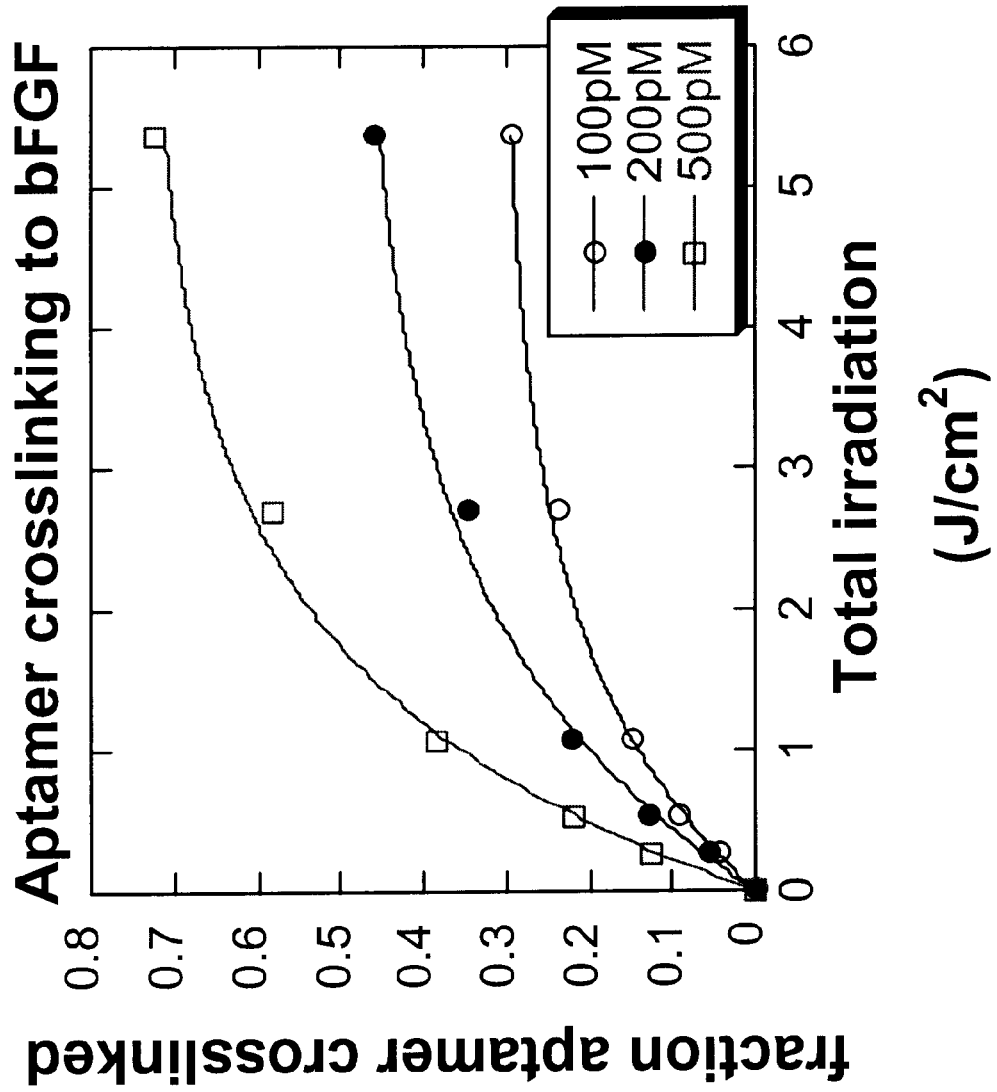
FIG. 15 depicts the fraction of aptamer crosslinked to bFGF plotted as a function of total irradiation ($J/cm^2$).

FIG. 14 depicts the increase in crosslinking as a function of irradiation and concentration. Briefly, an excess of protein (bFGF) was mixed with radiolabeled aptamer in a methacrylate cuvette and irradiated at 308 nm with a XeCl excimer laser at an intensity of 1. W/cm$^2$. At various points in the irradiation, samples were removed for analysis by denaturing PAGE. The fraction of aptamer crosslinked was then plotted as a function of total irradiation (FIG. 15). From these data, the initial rate of crosslinking of the 06.15 and 06.50 photoaptamers as a function of bFGF concentration were determined. The observed rates from each of these experiments were then plotted against bFGF concentration and the data fit to the following equation $$\text{fraction linked} = k_1 1(k_1+k_2) \times (1-e^{-(k1+k2)})$$

where $k_1$=the apparent first-order rate of crosslinking, $k_2$=the apparent first-order rate of photoinactivation and 1=total irradiation in J/cm$^2$ (FIG. 15). The second-order rate constants ($k_{xl}/K_M$) for each reaction were determined from these plots.

Crosslinking Specificity

A similar analysis was performed for the crosslinking of photoaptamers 06.15 and 06.50 to PDGF and thrombin. The results summarized in Table 5, show that these aptamers are markedly more active in crosslinking bFGF than PDGF or thrombin.

Effect of Crosslinking on Specificity

A key teaching of the present disclosure is that the crosslinking reaction adds to the specificity of aptamer-target interaction, allowing greater specificity to be achieved than through affinity binding alone. Table 6 combines the results of Table 7, which reports the specificity of affinity binding, with Table 5, which reports the specificity of the crosslinking reaction, and shows that the crosslinking reaction is always more specific than the binding reaction alone. The ability to enhance specificity by selecting for photocrosslinking ability is unique to the photoSELEX process.

The following examples are provided for illustrative purposes only and are not intended to limit the scope of the invention.

EXAMPLES

Materials

Recombinant human basic Fibroblast Growth Factor$_{155}$ (bFGF$_{155}$) expressed in *E. coli*, was purchased from Bachem California (Torrence, Calif.), Lot Number SN 433. The lyophilized protein was resuspended in 1×phosphate buffered saline (PBS) (Sambrook et al. (1989) *Molecular Cloning*, 2nd ed., Cold Spring Harbor Laboratory Press, Plainview, N.Y.), 2 mM MgCl$_2$, and 0.01% human serum albumin (HSA) to a concentration of 10 µM. Vascular Endothelial Growth Factor (VEGF) and Platelet Derived Growth Factor (PDGF) 1×PBS suspensions were obtained from R&D Systems (Minneapolis, Minn.). The DNA library, DNA ligands (06.50 and 06.15), and 5' and 3' primers (required for the polymerase chain reaction (PCR)) were prepared at NeXstar Pharmaceuticals, Boulder, Colo. (currently, NeXstar Division of Gilead Sciences, Inc.) on an Applied Biosystems Model 394 oligonucleotide synthesizer using established protocols. The 5' primer sequence was GGGAGGACGATGCGG (SEQ ID NO:1) and the 3' primer sequence was biotin-sp-biotin-sp-TCCCGCTCGTCGTCTG (SEQ ID NO:2). Unmodified deoxynucleoside triphosphates (dATP, dGTP and dCTP) were purchased as 10 mM glycerol suspensions from Pharmacia Biotech (Piscataway, N.J.). The modified deoxynucleoside triphosphate 5-bromo-2'-deoxyuridine-5'-triphosphate was purchased from Sigma Chemical Co. (St. Louis, Mo.) as a lyophilized sodium salt which was resuspended in deionized water to 10 mM. [γ-$^{32}$P] ATP used in T4 polynucleotide kinase 5' labeling of ssDNA was acquired from NEN Life Science Products (Boston, Mass.).

Example 1

Selection of Photo-Crosslinking Ligands to bFGF

Experimental details for ssDNA SELEX are described in Schneider et al. (1995) Biochemistry 34:9599–9610, which is incorporated herein by reference in its entirety and only special considerations relative to ssDNA PhotoSELEX are described herein. PCR amplification of a randomized 61 mer ssDNA library in which 5-BrdUTP was substituted for TTP was initially performed to generate sequences incorporating the chromophore. The PCR conditions for this non-crosslinked library employed a 1 mL reaction volume with a 1:1 mixture (12.5 units each) of Taq polymerase enzyme (Perkin Elmer Inc., Norwalk, Conn.) and Pwo polymerase enzyme (Boehringer-Mannheim Inc., Indianapolis, Ind.) in a standard Taq PCR buffer including 15 mM MgCl$_2$. Subsequent amplification of ligands identified as photocrosslinkers in each PhotoSELEX round employed identical PCR conditions except that limited and slightly perturbed template material mandated more PCR cycles to achieve sufficient yield. All amplifications were accomplished with a MJ Research Minicycler (Watertown, Mass.). To purify and isolate the sense ssDNA, the dsDNA was heated at 95° C. for 2 minutes and partitioned on a 12% polyacrylamide gel incorporating 7 M urea. The migration of the anti-sense strand was slowed due to the presence of two biotin groups covalently bound to the 3' primer, thus permitting ready separation.

Sense ssDNA was located on the polyacrylamide gel by UV shadowing and was subsequently excised and recovered by elution and NaOAc/ethanol precipitation. To facilitate identification of photocrosslinking ligands, 2 pmol of each recovered ssDNA library was 5'-radiolabeled with T4 polynucleotide kinase (PNK) (Boehringer-Mannheim) and purified on a 14% polyacrylamide gel. The position of the radiolabeled DNA was determined by 1.5 minute exposure of Kodak X-OMAT AR film (Eastman Kodak Co., Rochester, N.Y.). The radiolabeled band was excised and recovered as described above. These libraries were then subjected to the photocrosslinking reaction with bFGF$_{(155)}$.

The protocol started with a selection round employing 50 nM DNA, 25 nM bFGF$_{(155)}$ and 250 pulses of 308 nm light from an excimer laser. In each subsequent round, bFGF$_{(155)}$ concentration and the number of laser pulses were restricted in a stepwise fashion through the sixth round of selection which was completed with 50 nM DNA, 1.5 nM bFGF$_{(155)}$ and 30 laser pulses. For each round, 200 µL of radiolabeled 2×DNA was combined with 200 µL of 2×bFGF$_{(155)}$ and incubated at 37° C. for 15 minutes. This mixture was placed in a 1.5 mL semi-micron methacrylate cuvette possessing a 1 cm path length (Fisher Scientific Co., Pittsburgh, Pa.) and irradiated at 37° C. for the number of laser pulses indicated above. Photocrosslinking reactions used for screening, for maximizing crosslink yield, and for evaluating diagnostic potential were also conducted in this way.

Partitioning of sequences capable of photocrosslinking with bFGF$_{(155)}$ from those incapable of such crosslinking was accomplished by polyacrylamide gel electrophoresis (PAGE). Specifically, the crosslink reaction volume was reduced by centrifugation through a 30 k MWCO Centri-Sep filter at 12,000 rpm/15 min. Crosslinked oligonucleotide/protein adducts, non crosslinked ssDNA, unreacted bFGF$_{(155)}$, and photo-damaged ssDNA were all recovered from the filter by washing with the formamide gel loading buffer and subsequently partitioned via 12% PAGE with 7 M urea. As bFGF$_{(155)}$ and 61-nt ssDNA sequences are both ≈18 kDa, crosslinked DNA migrated in the gel about half as fast as free DNA. The crosslinked material was excised from the gel and then crushed to a slurry in 400 μL of proteinase K buffer (0.1 M Tris/pH 7.5, 0.05 M NaCl, 0.02 M EDTA, 0.5% SDS).

The protein portion of each oligonucleotide/protein crosslinked adduct was reduced by proteinase K digestion. This was accomplished by adding 100 μL of 4 mg/mL proteinase K in buffer to each 400 μL gel slurry containing the crosslinked adduct and incubating at 48° C. for 75 minutes. To promote digestion, 50 μL of 7 M urea was then added and the mixture was incubated for an additional 15 minutes at 48° C. After this period of incubation two more additions of 100 μL of 7 M urea and 15 minute incubations at 48° C. were completed. This yielded crosslinking oligonucleotide templates suitable for amplification by PCR. The digested adduct was then extracted with phenol/chloroform to remove enzyme and amino acids from the oligonucleotides and concentrated by NaOAc/EtOH precipitation to complete one round of PhotoSELEX. Prior to initiation of each subsequent round of Photo SELEX, a pilot PCR using 5'-$^{32}$P-radiolabeled primer and the 1:1 mixture of Taq and Pwo polymerase enzymes was performed to identify the number of cycles which would give maximum PCR amplification (typically 16–23 cycles). Half of the recovered oligonucleotide sample from the previous round was then used for PCR amplification to generate the new library. Monitoring PhotoSELEX evolution was accomplished by measuring photocrosslink yield and binding affinity screening. Upon convergence to a library of less than 100 different sequences after six rounds of selection, the evolved ligands were cloned and sequenced (see Table 1, SEQ ID NOS:4–98). Based upon results of screening for affinity and crosslink yield two ligands, designated as ligand 06.15 (SEQ ID NO:71) and 06.50 (SEQ ID NO:70), were selected for evaluation as diagnostics for bFGF$_{(155)}$.

Example 2
Evaluation of Ligand Sensitivity

PCR amplification of 15 pmol of ssDNA with 5-BrdUTP substituted for TTP was performed using the methodology described in Example 1 to generate sufficient quantities of both ligands bearing the chromophore to evaluate their diagnostic potential. The ligands were then 5'-$^{32}$P-radiolabeled as described above.

Nitrocellulose filter binding was used to assess ligand affinity for bFGF$_{(155)}$. This was accomplished by first preparing 2,000 cpm/30 μL of 5'-$^{32}$P-radiolabeled material (≈1–5 fmol) of each sequence by dilution with 1×crosslink binding buffer (XLBB) (1×PBS/2 mM MgCl$_2$/0.01% HSA/1.0 mM dithiothreitol (DTT)) to give 2×DNA. Each 2×oligonucleotide sample was mixed with 30 μL of each bFGF$_{(155)}$ concentration to be evaluated in a 96 well tray. bFGF$_{(155)}$ concentrations were prepared by serial dilution with 1×XLBB. After incubation at 37° C. for 15 minutes, a multi-pipeter was used to load 40 μL of each DNA/bFGF$_{(155)}$ mixture onto a pre-washed Gibco nitrocellulose binding curve apparatus followed by washing with a dissociation wash buffer. Bound DNA was then measured by phosphorimage and a binding curve for the percent bound DNA vs. [bFGF] was calculated by Kaleidograph ver. 3.09 software (Synergy Software Co., Reading, Pa).

Photocrosslink yield was measured by preparing 50 μL of 2,000 cpm/μL of 5'-$^{32}$p-radio-labeled material (-≈1–5 fmol) of each sequence by dilution with 1×XLBB (2×DNA). These were combined with 50 μL of 50 nM bFGF$_{(155)}$ and placed in separate 1.5 mL methacrylate cuvettes possessing a 1 cm path length. The cuvettes were subsequently placed in a 37° C. cuvette holder and incubated for 15 minutes. Each cuvette was then irradiated with 1500 pulses of 308 nm light generated by a Lumonix Model EX 700 XeCl excimer laser. The time of irradiation was specified by the number of 20 ns pulses delivered to the sample. The laser was set to deliver 20 such pulses per second with a total pulse energy of 175 mJ. Each laser pulse was attenuated by passing through a quartz convex lens with the result that each sample received approximately 11 mJ/pulse of 308 nm light. In each reaction a 20 μL aliquot was removed and mixed with 20 μL of 2×SDS gel loading buffer (0.1 M Tris-Cl/pH 6.8, 0.2 M DTT, 4% SDS, 2×dye (40% glycerol, 0.4% bromophenol blue, 60% water)). These mixtures were heated at 95° C. for 3 minutes and loaded on a 5% SDS-Stacking PAGE/12% SDS-Resolving PAGE (Sambrook et al. (1989) *Molecular Cloning*, 2nd ed., Cold Spring Harbor Laboratory Press, Plainview, N.Y.). The crosslink signal was then assessed by exposing the gel to a phosphor-image plate for 30 minutes with subsequent radiation counting accomplished with Fujix MacBas ver. 2.0 software (FujiPhoto Film Co., Stamford, Conn).

Absolute ligand sensitivity was assessed by performing a photochemical analog to the thermal binding curve. This was accomplished by preparing photocrosslinking reactions as described above except that the various 2×bFGF$_{(155)}$ concentrations were prepared by serial dilution with 1×XLBB. All other steps were performed precisely as described above for measurement of photocrosslink yield.

Example 3 Evaluation of Ligand Specificity

Nitrocellulose filter binding was used to assess ligand affinity for both VEGF and PDGF, using the method described above for ligand affinity for bFGF$_{(155)}$. The calculated dissociation constants were then normalized with the results previously obtained for bFGF$_{(155)}$.

Photocrosslinking specificity was measured by performing the photochemical analog to the thermal binding curve in a 10% serum crosslinking medium. This experiment was performed as described above for determination of photocrosslink yield with two exceptions. First, various 2×bFGF$_{(155)}$ concentrations were prepared by serial dilution. Second, the diluting medium for both 5'-$^{32}$P-radiolabeled material and bFGF$_{(155)}$ was composed of 10% serum/90% 1×XLBB. All other steps were performed precisely as described above for measurement of photocrosslink yield. Finally, photocrosslinking specificity was determined by measuring the photocrosslink yield of both 06.15 and 06.50 with VEGF and PDGF. These reactions were completed and evaluated as described above for determination of photocrosslink yield of these ligands with bFGF$_{(155)}$.

Figure 5:
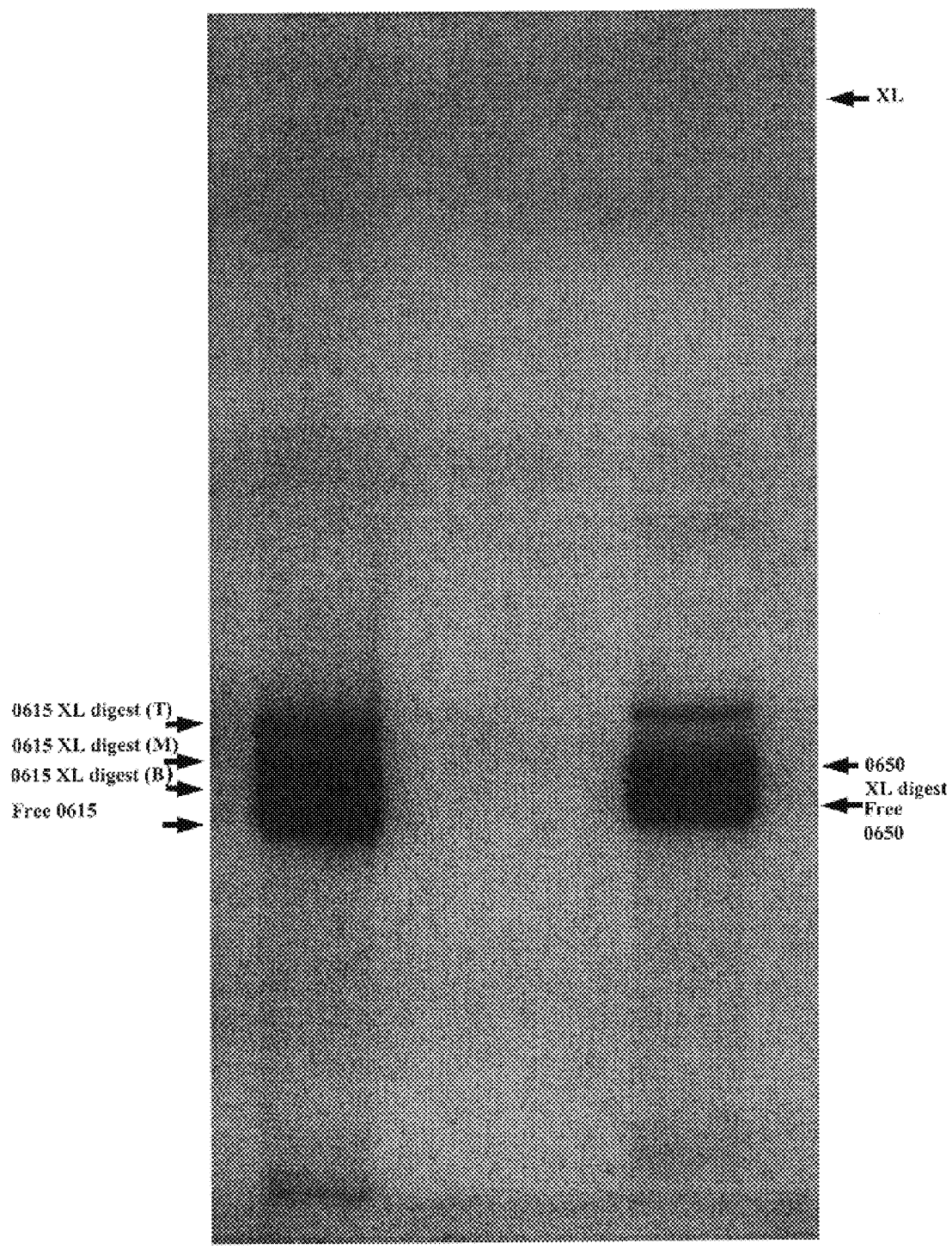
FIG. 5 illustrates the denaturating PAGE of trypsin-digested ligands 0.615 and 0.650/bFGF crosslinked adducts.

Example 4
Determination of the bFGF Crosslinking Amino Acid by Edman Degradation In order to produce sufficient crosslink material of tractable peptide length for Edman degradation, 850 pmol with 1,000 cpm/μL specific activity 5'-$^{32}$P-labeled ligand 06.50 and 06.15 were crosslinked with 283.3 pmol of bFGF in a 1 mL reaction volume using 1500 pulses of 308 nm light. The reaction mixture was subsequently digested with a large excess of trypsin, extracted with phenol/chloroform and partitioned by denaturing PAGE. The results of this procedure are shown in FIG. 5. With reference to FIG. 5, it can be seen that no band appears in the standard crosslink migration region. However, for both ligands, bands which migrate slightly slower than free DNA do appear. These bands correspond to bFGF tryptic fragments, which include the crosslinking amino acid covalently bound to full length 06.50 and 06.15. It is interesting that multiple slightly-slower migrating bands appear for both sequences. In the case of ligand 06.15, this effect is particularly apparent. These results can be interpreted as a consequence of the bulky oligonucleotide interfering with trypsin's ability to cleave efficiently after all Lys/Arg residues. This observation is consistent with the conclusion of Gospodarowicz and Cheng (1986) J. Cell Physiol 128:475–484 and Saksela et al. (1998) J. Cell Biol. 107:743–751, who observed that heparin protects bFGF against enzymatic digestion.

The large ligand 06.50/bFGF tryptic fragment band, and all three of the ligand 06.15/bFGF tryptic fragment bands were excised and eluted from the gel with an estimate of the quality of recovered material based upon specific activity. Finally, approximately 60 pmol of 06.50/bFGF tryptic fragment and 30 pmol of each 06.15/bFGF tryptic fragment were submitted for Edman degradation sequencing with the following results:

(SEQ ID NO:70)
ligand 06.50

Arg-Thr-Gly-Gln-___-Lys-Leu-Gly-Ser-Lys (SEQ ID NO:76)
ligand 06.15

Gln-___-Lys-Leu-???-Ser(Top)

Gln-___-Lys-Leu (Middle)

Gln-___-Lys(Bottom).

Example 5
Determination of the bFGF Crosslinking Amino Acid by Mass Spectrometry To evaluate the potential for ESMS sequencing to identify the crosslinking amino acid in bFGF, trypsin digested ligand 06.50/bFGF crosslinked adduct was prepared as described in Example 4 for Edman degradation sequencing. Once obtained, the oligonucleotide component (still full length 61-mer) of the crosslinked adduct needed to be substantially reduced. This is desirable in order to utilize the positive ion mode of the ESMS (oligonucleotides generate negative ions while peptides generate positive ions in ESMS), and to reduce potential noise from unwanted oligonucleotide fragmentation. To accomplish this, 60 pmol trypsin-digested ligand 06.50/bFGF crosslinked adduct was digested with snake venom phosphodiesterase (SVP) and alkaline phosphatase (AP). SVP digests oligonucleotides into mononucleotides by sequentially cleaving the phosphodiester bond at the 5' and 3' ends of an oligonucleotide. AP removes PO$_4^{3-}$ on the 3' and 5' ends of nucleotides by hydrolyzing them to hydroxyl groups. SVP/AP digestion of tryptic 06.50/bFGF should then yield a small nucleotide fragment (e.g., mono, di or triucleotide) cross-linked to a small peptide fragment (e.g., the fragment identified by Edman degradation).

Figure 7:
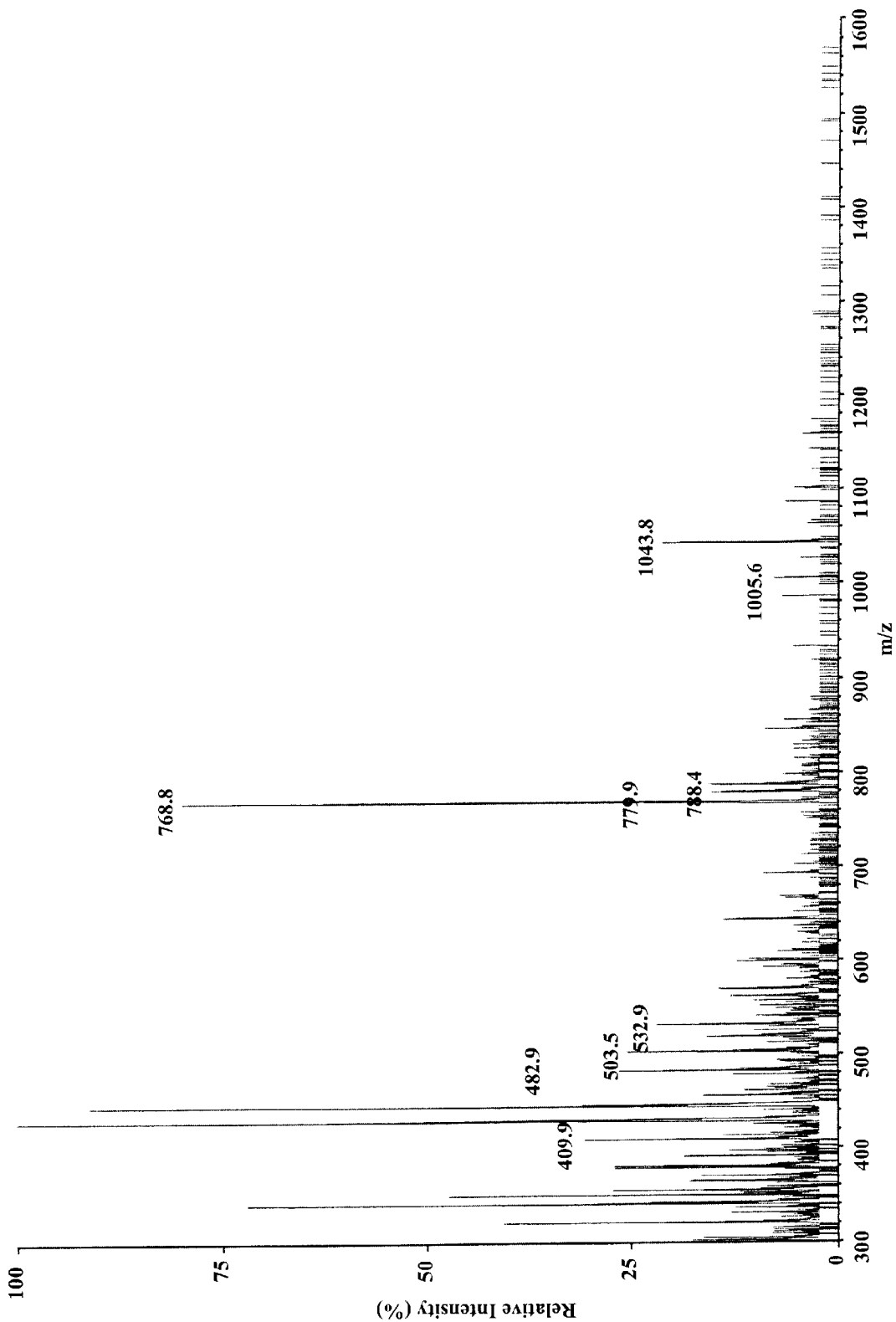
FIG. 7 depicts the ESMS of ligand 06.50/bFGF SVP/AP tryptic fragment. The adduct's molecular weight was determined to be 1537 (2×768.8).
Figure 8:
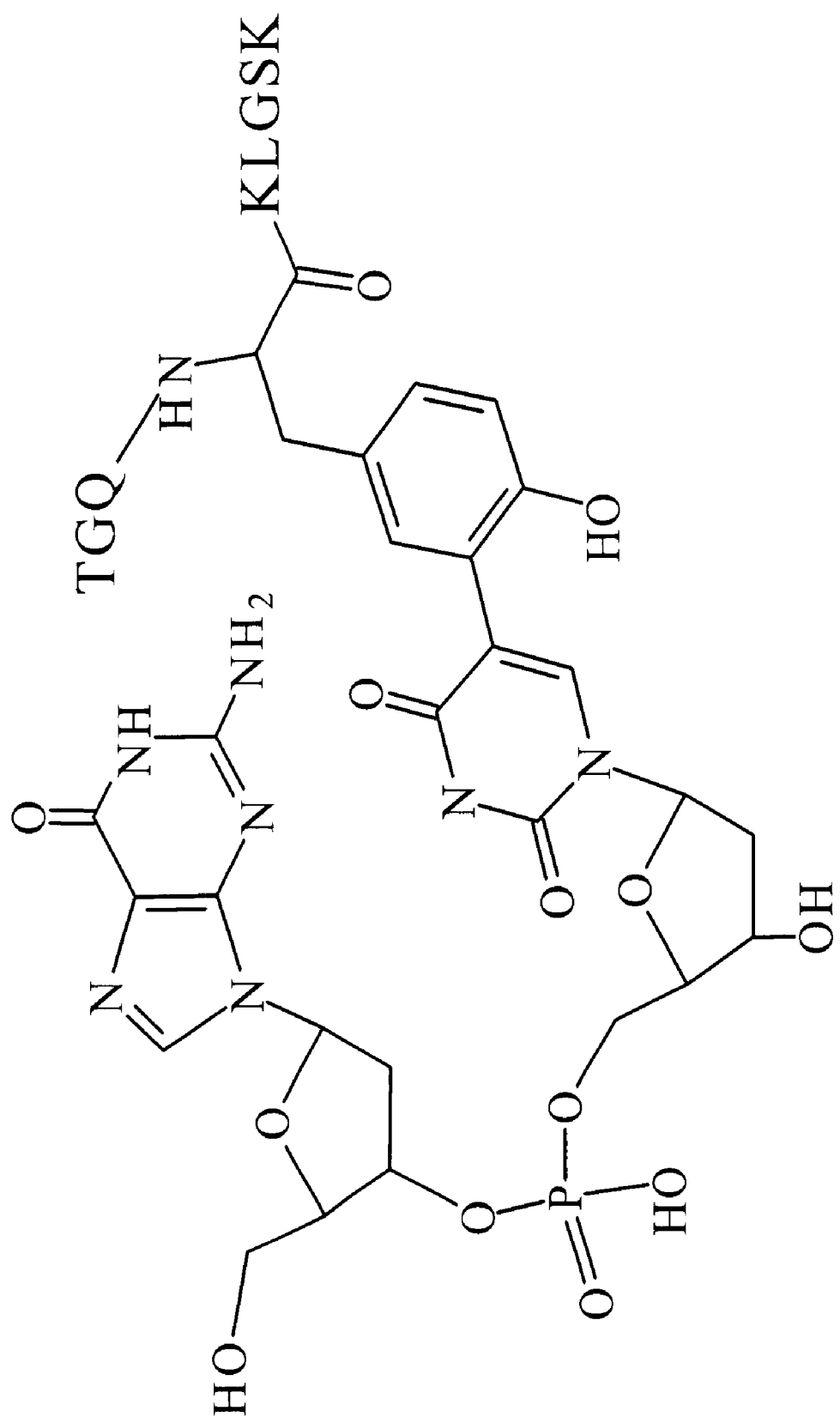
FIG. 8 illustrates the GU (minus uracil's 5'-H) dinucleotide cross-linked to bFGF nonapeptide.

Finally, 20 pmol of the SVP/AP/tryptic digested 06.50/bFGF crosslinked fragment was loaded onto an HPLC equipped ESMS/MS. ESMS showed a substantial peak at m/z 768.8 as shown in FIG. 7. This peak was substantially determined to be a doubly-charged ion due to the presence of the nearby peak of m/z 779.9. The peak at 779.9 is a result of the molecular ion associated with Na$^+$ in place of H$^+$. This alteration should result in an increase of m/z of 22. However, it appears as an increase in m/z of 11—half of that expected and thus the molecular ion must be doubly charged. As a result, this parent ion has a singly-charged m/z of 1537. This corresponds to a GU (minus uracil's 5'-H) dinucleotide covalently bound to Tyr within the nonapeptide fragment TGQNYKLGSK having the structure as illustrated in FIG. 8.

Figure 9:
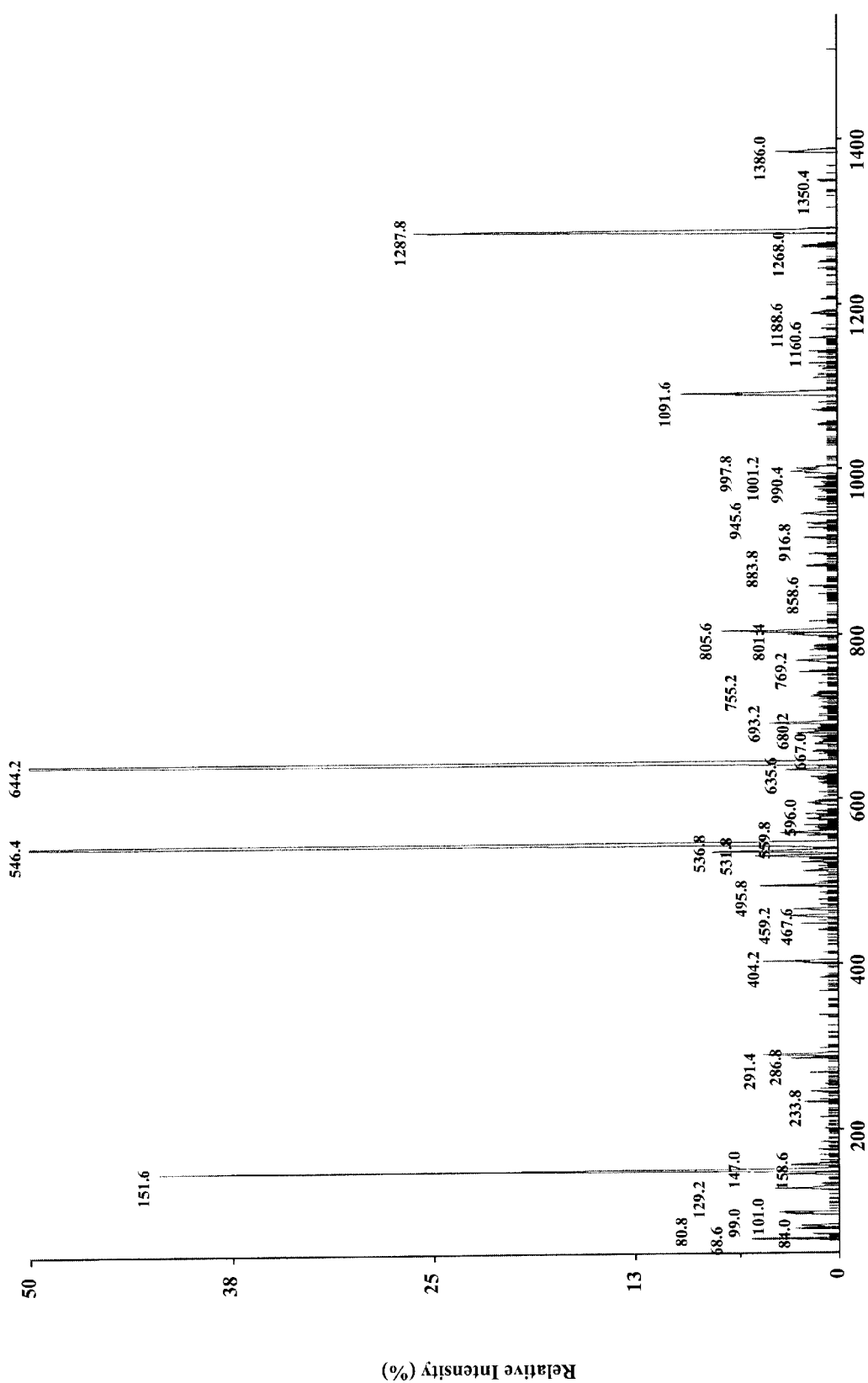
FIG. 9 illustrates the MS-MS of molecular ion 768.8 m/z.

In order to confirm this as the structure of the molecular ion resulting from SVP/AP/trypsin digestion of the 06.50/bFGF crosslinked adduct, this ion was subjected to MS-MS. FIG. 9 shows the resulting mass spectrum.

Figure 10:
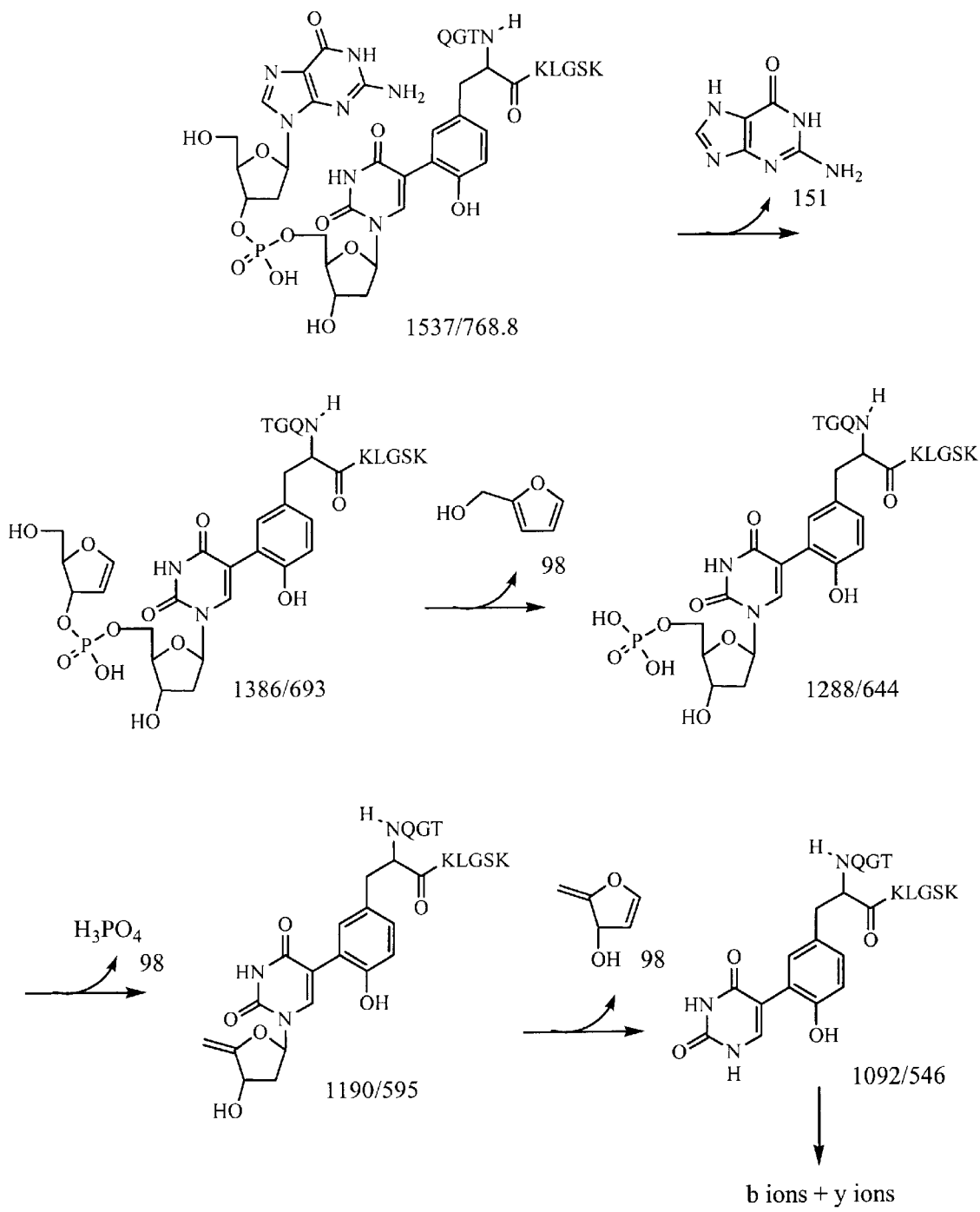
FIG. 10 illustrates the mass spectrometric fragmentation of daughter ions from SVP/AP/trypsin digested 06.50/bFGF crosslinked adduct.
Figure 11:
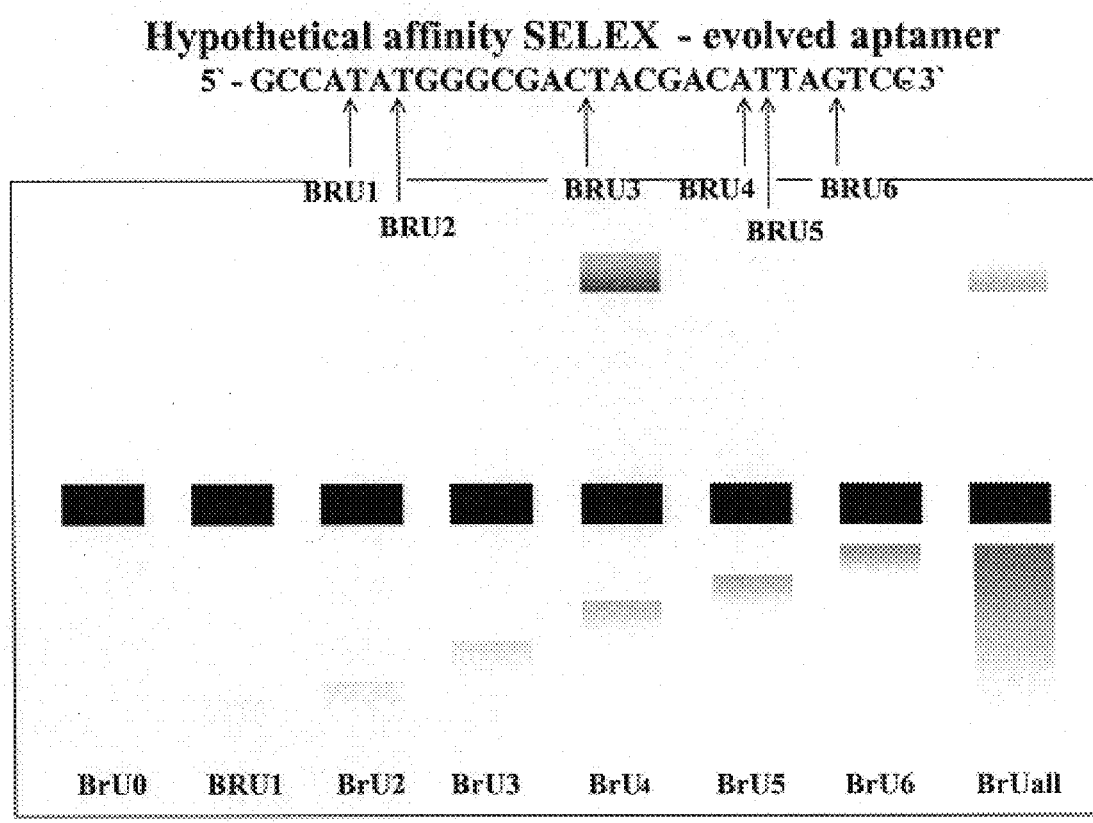
FIG. 11 illustrates the single substitution experiment to identify the crosslinking position of a post-affinity SELEX modified ligand.

FIG. 10 depicts the daughter ions resulting from EI bombardment of this putative adduct. The corresponding m/z for these structure coincides exceedingly well with peaks in FIG. 9. As shown in FIG. 10, fragmentation continues until the daughter ion with m/z 1092 (uracil base minus the 5'H covalently bound to nonapeptide fragment) is generated. This daughter ion is sufficiently stable to permit generation of the ABC/XYZ ions resulting from peptide backbone bond cleavage with subsequent peptide sequencing possible. The results are shown in Table 4. As can be seen, the m/z of the b and y-ions produced as N and C-terminal fragments correspond precisely to that expected from the non-post-translationally modified nonapeptide bFGF fragment until the Tyr residue is reached. The mass of the crosslinked residue at this position is 110 m/z greater than the free y6 ion would be. This is precisely the mass of the uracil cross-linked to tyrosine minus 2H (one H from the 5' position of uracil which was originally bonded to BrdU and one H from a position of the new covalent bond). These results confirm Tyr133 as bFGF's crosslinking amino acid to the 06.50 ligand (see FIG. 11).

TABLE 1

Sequences of BrdU aptamers for bFGF from the 5xA/6xP hv * library
(T = BrdU)
gggaggacgatgcgg|30N|cagacgacgagcggga (SEQ ID NO:3)

| | | SEQ ID NO: |
|---|---|---|
| Family I | | |
| 56hv.6 | tgcggTGACGTAAGAGTGTAATCGATGCAGCCTGGcagacgacgagcg | 4 |
| 56hv.49 | tgcggTGACGTAAGAGTGTAATCGATGCAGCCTGGcagacgacgagcg | 5 |
| 56hv.30 | tgcggTGACGTAAGAGTGTAATCGATGCAGCCTGGcagacgacgagcg | 6 |
| 56hv.m1 | tgcggTGACGTAAGAGTGTAATCGATGCAGCCTGGcagacgacgagcg | 7 |
| 56hv.m7 | tgcggTGACGTAAGAGTGTAATCGATGCAGCCTGGcagacgacgagcg | 8 |
| 56hv.m12 | tgcggTGACGTAAGAGTGTAATCGATGCAGCCTGGcagacgacgagcg | 9 |
| 56hv.m15 | tgcggTGACGTAAGAGTGTAATCGATGCAGCCTGGcagacgacgagcg | 10 |
| 56hv.m22 | tgcggTGACGTAAGAGTGTAATCGATGCAGCCTGGcagacgacgagcg | 11 |
| Family II | | |
| 56hv.8 | tgcggACCACAGCGCTGATGG TTCATACTATTCCGca | 12 |
| 56hv.14 | tgcggACCACAGCGCTGATGG TTCATACTATTCCGca | 13 |
| 56hv.15 | tgcggACCACAGCGCTGATGG TTCATACTATTCCGca | 14 |
| 56hv.m20 | tgcggCCAAGGTGACATCCGGG TTCATAGTATCCGca | 15 |
| 56hv.29 | GCCGAAGTGACACGAGG TTCATAGTATGCC | 16 |
| 56hv.m11 | tgcggCGCAAGCAAACGCTGAG TTCATAGTATCCGca | 17 |
| 56hv.7 | tgcggACCACAGCGATGATGG TTCATATTATTCCAca | 18 |
| 56hv.20 | tgcggACCACAGCGATGATGG TTCATATTATTCCAca | 19 |
| 56hv.m4 | tgcggGCGAAGTCATTCACGAG TTCATCATATCCCcaga | 20 |
| 56hv.2 | GCAAAGTTCTACGAG TTCATCTTATCCCAA | 21 |
| 56hv.m23 | GCAAAGTTCTACGAG TTCATCTTATCCCAA | 22 |
| 56hv.41 | GCAAAGTTCTACGAG TTCATCTTATCCCAA | 23 |
| 56hv.11 | tgcggGCCAAGGGTCTCACGG TTCATTCTATCCCAca | 24 |
| 56hv.50 | ggGGCAAGCCAACGCGTG TTCATTGTATCCCC | 25 |
| 56hv.46 | tgcggCAAAGACATACTGGAGG TTCACTTTATCCGca | 26 |
| 56hv.32 | ACCAAAGCCAGCGGG TTACATACTATCCTG | 27 |
| 56hv.26 | GTACGAAGGCGACCCGAG TTAATCTTACCC | 28 |
| 56hv.33 | ACATGAAGCTACTGCGAC TTAAATCTTGGC | 29 |
| 56hv.m21 | GAACAAAGGCGCCCGTGTA TTTTCTTTCCC | 30 |
| 56hv.38 | GAACAAAGGCGCCCGTGTA TTTTCTTTCCC | 31 |
| 56hv.4 | CGAGCGGAGACG TTTTATTATCCA | 32 |
| 56hv.17 | CGAGGTAGGCCAG TTTTATTATCA | 33 |
| Family I | | |
| 56af.6 | tgcggTGACGTAAGAGTGTAATCGATGCAGCCTGGcagacgacgagcg | 34 |
| 56af.13 | tgcggTGACGTAAGAGTGTAATCGATGCAGCCTGGcagacgacgagcg | 35 |
| 56af.15 | tgcggTGACGTAAGAGTGTAATCGATGCAGCCTGGcagacgacgagcg | 36 |
| 56af.32 | tgcggTGACGTAAGAGTGTAATCGATGCAGCCTGGcagacgacgagcg | 37 |
| 56af.36 | tgcggTGACGTAAGAGTGTAATCGATGCAGCCTGGcagacgacgagcg | 38 |
| 56af.38 | tgcggTGACGTAAGAGTGTAATCGATGCAGCCTGGcagacgacgagcg | 39 |
| Family II | | |
| 56af.19 | tgcggACCACAGCGCTGATGG TTCATACTATTCCGca | 40 |
| 56af.20 | tgcggACCACAGCGCTGATGG TTCATACTATTCCGca | 41 |
| 56af.45 | tgcggACCACAGCGCTGATGG TTCATACTATTCCGca | 42 |
| 56af.47 | tgcggACCACAGCGCTGATGG TTCATACTATTCCGca | 43 |
| 56af.37 | CAGGCTACCACAGTACCGAG TTCATACTAT | 44 |
| 56af.40 | CAACCACTGGGGCTTG TTCATAGTATCCGC | 45 |
| 56af.25 | GCCGAATCATTGGAGAG TTCATAGTATGCCC | 46 |
| 56af.22 | CGAAGGGACAACCCTAC TTCATAATATCCG | 47 |
| 56af.3 | GCCGAAGTTCTAACGCG TTCATCCTATGCC | 48 |
| 56af.21 | GCCGAAGTTCTAACGCG TTCATCCTATGCC | 49 |
| 56af.16 | GTCGAAGCCATGCAAG TTCATTGTATACCC | 50 |
| 56af.41 | GTCGAAGCCATGCAAG TTCATTGTATACCC | 51 |
| 56af.23 | CGAAGGTCACCGAG TTCTATGCTATCCGCA | 52 |
| 56af.30 | CGAAGGTCACCGAG TTCTATGCTATCCGCA | 53 |
| 56af.4 | CGAAGGTCACCGAG TTCTGTGCTATCCGCA | 54 |
| 56af.17 | CCGGAGGTCTCCAAG TTCATTACTATGCCA | 55 |
| 56af.5 | GACGAAGGCGTCCGAG TTCAATCTTCCCAG | 56 |
| 56af.27 | GACGAAGACGTGCGAG TTGAATCTTCCCAG | 57 |
| 56af.29 | GACGAAGGCGTCCGAG TTGAATCTTCCCAG | 58 |
| 56af.1 | ggCCACGAAGGCGACCCGAG TTTCATCTTGGCc | 59 |
| 56af.46 | ggCCACGAAGGCGACCCGAG TTTCATCTTGGCc | 60 |
| 56af.12 | GCCGAAGTTCTAACGCG TTTATCCTATGCC | 61 |
| 56af.2 | CGAAAGGCAACCCGAG TTTATAGTATCCAG | 62 |
| 56af.26 | GCGAAGGCACACCGAG TTTATAGTATCCCA | 63 |

* The ssDNA library evolve from five rounds of affinity selection and six rounds of covalent selection (5xA/6xP).

TABLE 2

Sequences of BrdU aptamers for bFGF from the 0xA/6xP * library
(T = BrdU)
gggaggacgatgcgg|30N|cagacgacgagcggga (SEQ ID NO:3)

| | | SEQ ID NO: |
|---|---|---|
| Family I | | |
| 06.24 | tgcggTGACGTAAGAGTGTAATCGATGCAGCCTGGcagacgacagcg | 64 |
| 06.30 | tgcggTGACGTAAGAGTGTAATCGATGCAGCCTGGcagacgacagcg | 65 |
| 06.32 | tgcggTGACGTAAGAGTGTAATCGATGCAGCCTGGcagacgacagcg | 66 |
| 06.36 | tgcggTGACGTAAGAGTGTAATCGATGCAGCCTGGcagacgacagcg | 67 |
| 06.45a | tgcggTGACGTAAGAGTGTAATCGATGCAGCCTGGcagacgacagcg | 68 |
| 06.49 | tgcggTGACGTAAGAGTGTAATCGATGCACCCTGGcagacgacagcg | 69 |
| 06.50 | tgcggTGACGTAAGAGTGTAATCGATGCACCCTGGcagacgacagcg | 70 |
| 06.58 | tgcggTGACGTAAGAGTGTAATCGATGCACCCTGGcagacgacagcg | 71 |
| Family II | | |
| 06.1 | tgcggACCACAGCGCTGATGG TTCATACTATTCCAca | 72 |
| 06.43 | tgcggACCACAGCGCTGATGG TTCATACTATTCCAca | 73 |
| 06.3 | tgcggACCAAAGGCAATCCGGG TTCATACTATTCCcaga | 74 |
| 06.53 | tgcggACCAAAGGCAATCCGGG TTCATACTATTCCcaga | 75 |
| 06.15 | tgcggGCGAAGGCACACCGAG TTCATAGTATCCCAca | 76 |
| 06.19 | tgcggGCGAAGGCACACCGAG TTCATAGTATCCCAca | 77 |
| 06.41 | tgcggGCGAAGGCACACCGAG TTCATAGTATCCCAca | 78 |
| 06.10 | tgcggCGCAAGCAAACGCTGAG TTCATAGTATCCGca | 79 |
| 06.44 | tgcggCGCAAGCAAACGCTGAG TTCATAGTATCCGca | 80 |
| 06.55 | tgcggCGCAAGCGAACGCTGAG TTCATAGTATCCGca | 81 |
| 06.12 | gTGACGAAGGCTACCGAG TTCATATTATTCAc | 82 |
| 06.17 | tgcggCGAAGGCTACCTCCAAG TTCATATTATCCGca | 83 |
| 06.20 | GGCCATGTCTCATAG TTCATATTATACCTG | 84 |
| 06.59 | GGCCATGTCTCATAG TTCATATTATACCTG | 85 |
| 06.35 | ggGCCGAAGTTCTAACGCG TTCATCCTATGCCc | 86 |
| 06.52 | ggGCCGAAGTTCTAACGCG TTCATCCTATGCCc | 87 |
| 06.57 | ggGCCGAAGTTCTAACGCG TTCATCCTATGCCc | 88 |
| 06.5 | tgcggCGAAGGTCACCGAG TTCTATGCTATCCGCA | 89 |
| 06.11 | tgcggCGAAGGTCACCGAG TTCTATGCTATCCGCA | 90 |
| 06.18 | tgcggCGAAGGTCACCGAG TTCTATGCTATCCGCA | 91 |
| 06.7 | ggCCACGAAGGCGACCCGAG TTTCATCTTGGCc | 92 |
| 06.22 | ggCCACGAAGGCGACCCGAG TTTCATCTTGGCc | 93 |
| 06.31 | ggCCACGAAGGCGACCCGAG TTTCATCTTGGCc | 94 |
| 06.60 | ggCCACGAAGGCGACCCGAG TTTCATCTTGGCc | 95 |
| 06.28 | ggGACGAAGGCGCCCGAG TTGAATCTTCCCAG | 96 |
| 06.29 | ggGACGAAGGCGCCCGAG TTGAATCTTCCCAG | 97 |
| 06.38 | ggGACGAAGGCGCCCGAG TTGAATCTTCCCAG | 98 |

* The ss DNA library evolved from zero rounds of affinity selection and six rounds of covalent selection (0xA/6xP).

TABLE 3

Specificity of ligands 06.15 and 06.50 for bFGF$_{(155)}$

| | Relative K$_D$ | | | |
|---|---|---|---|---|
| Ligand | bFGF | VEGF | PDGF | Thrombin |
| 06.15 | 1 | >1000 | >1000 | >1000 |
| 06.50 | 1 | >1000 | 53 | >1000 |

TABLE 4 m/z of the b and y-ions resulting from EI fragmentation of 1092 m/z ion

| N-Terminal Fragments | | | | C-Terminal Fragments | | | |
|---|---|---|---|---|---|---|---|
| n | a | b | c | n | x | y | z |
| 0 | — | 1.01 | 16.02 | 9 | — | 1091.55 | 1074.52 |
| 1 | 74.06 | 102.06 | 117.07 | 8 | 1016.48 | 990.50 | 973.47 |
| 2 | 131.08 | 159.08 | 174.09 | 7 | 959.46 | 933.48 | 916.45 |
| 3 | 259.14 | 287.14 | 302.15 | 6 | 831.40 | 805.42 | 788.39 |
| 4 | 532.22 | 560.21 | 575.22 | 5 | 558.33 | 532.35 | 515.32 |
| 5 | 660.31 | 688.31 | 703.32 | 4 | 430.23 | 404.25 | 387.22 |
| 6 | 773.39 | 801.39 | 816.40 | 3 | 317.15 | 291.17 | 274.14 |
| 7 | 830.42 | 858.41 | 873.42 | 2 | 260.12 | 234.15 | 217.12 |
| 8 | 917.45 | 945.44 | 960.45 | 1 | 173.09 | 147.11 | 130.09 |
| 9 | 1045.54 | 1073.54 | — | 0 | 45.00 | 19.02 | — |

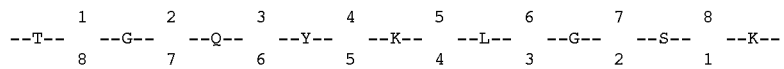

TABLE 5

Crosslinking Specificity

|  | bFGF | PDGF | Thrombin |
|---|---|---|---|
| 06.15 rate ($M^{-1}s^{-1}$) | $1.6 \times 10^9$ | $6.5 \times 10^4$ | $2.2 \times 10^3$ |
| bFGF/non-target | — | $2.5 \times 10^4$ | $7.3 \times 10^5$ |
| 06.50 rate ($M^{-1}s^{-1}$) | $1.9 \times 10^9$ | $6.1 \times 10^4$ | $1.8 \times 10^3$ |
| bFGF/non-target | — | $3.1 \times 10^4$ | $1.6 \times 10^6$ |

TABLE 6

Binding Specificity

|  | PDGF | Thrombin |
|---|---|---|
| 06.15 crosslink specificity | $2.5 \times 10^4$ | $7.3 \times 10^5$ |
| 06.15 affinity specificity | 1500 | $1.1 \times 10^5$ |
| crosslinking/affinity | 17 | 7 |
| 06.50 crosslink specificity | $3.1 \times 10^4$ | $1.0 \times 10^6$ |
| 06.50 affinity specificity | 53 | $>2.5 \times 10^5$ |
| crosslinking/affinity | 580 | <4 |

TABLE 7

Contribution of Crosslinking to specificity

|  | bFGF | PDGF | Thrombin |
|---|---|---|---|
| 06.15 $K_D$, M | $1.3 \times 10^{-10}$ | $2.0 \times 10^{-7}$ | $1.4 \times 10^{-5}$ |
| bFGF/non-target | — | $1.5 \times 10^3$ | $1.1 \times 10^{-5}$ |
| 06.50 $K_D$, M | $5.3 \times 10^{-9}$ | $2.8 \times 10^{-7}$ | $>1.0 \times 10^{-3}$ |
| bFGF/non-target | — | 53 | $>2.3 \times 10^5$ |

---

What is claimed is:

1. A method for detecting the presence or absence of a peptide or protein target molecule in a sample which may contain said target molecule comprising:
    a) exposing said sample which may contain said target molecule to a non-naturally occurring photoaptamer of said target molecule, under conditions wherein a target molecule:photoaptamer complex is formed if said target molecule is present, wherein said complex is not due to Watson/Crick base pairing;
    b) irradiating said complexes, wherein said target molecule and photoaptamer photocrosslink; and
    c) determining whether said target molecule:photoaptamer crosslink is formed, thereby detecting the presence or absence of the target molecule in the sample.

2. The method of claim 1 wherein said photoaptamer is a single-stranded nucleic acid ligand.

3. The method of claim 2 wherein said single-stranded nucleic acid ligand is ribonucleic acid.

4. The method of claim 2 wherein said single-stranded nucleic acid ligand is deoxyribonucleic acid.

5. The method of claim 1 wherein said photoaptamer is labeled.

6. The method of claim 5 wherein said label is a radiolabel.

7. The method of claim 1 wherein said protein is not known to bind nucleic acids as part of its biological function.

8. The method of claim 1 wherein said target molecule is a controlled substance.

9. The method of claim 1 wherein said target molecule is a metabolite.

10. The method of claim 1 wherein said sample is a biological substance.

11. The method of claim 1 wherein said detection comprises
    a) separating the target and the photoaptamer to a level sufficient for amplification of the photoaptamer by PCR;
    b) amplifying the photoaptamer by PCR; and
    c) detecting the amplified photoaptamer; whereby the presence or absence of the target molecule in the sample is detected.

12. A method for detecting the presence or absence of a protein or peptide target molecule in a sample which may contain said target molecule comprising:
    a) identifying a photoaptamer from a candidate mixture of photoaptamers, said photoaptamer being a ligand of said target molecule, by a method comprising:
        i) contacting the candidate mixture with said target molecule, wherein photoaptamers having an increased affinity to said target molecule relative to the candidate mixture form photoaptamer-target complexes;
        ii) irradiating said complexes, wherein said target molecule and photoaptamer photocrosslink;
        iii) partitioning the photocrosslinked photoaptamer-target complexes from the remainder of the candidate mixture; and
        iv) amplifying the photocrosslinked photoaptamers to yield a ligand-enriched mixture of photoaptamers, whereby an increased affinity photoaptamer may be identified;
    b) exposing said sample which may contain said target molecule to said increased affinity photoaptamer of said target molecule under conditions wherein a target molecule:photoaptamer complex is formed if said target molecule is present;

c) irradiating said complex, wherein said target molecule and photoaptamer photocrosslink; and d) determining whether said target molecule:photoaptamer photocrosslink is formed, thereby detecting the presence or absence of the target molecule in the sample.

13. The method of claim 12 further comprising:

iv) repeating steps i), ii), iii) and iv).

14. The method of claim 12 wherein said photoaptamer is a single-stranded nucleic acid ligand.

15. The method of claim 14 wherein said single-stranded nucleic acid ligand is ribonucleic acid.

16. The method of claim 14 wherein said single-stranded nucleic acid ligand is deoxyribonucleic acid.

17. The method of claim 12 wherein said protein is not known to bind nucleic acids as part of its biological function.

18. The method of claim 12 wherein said target molecule is a controlled substance.

19. The method of claim 12 wherein said target molecule is a metabolite.

20. The method of claim 12 wherein said sample is a biological substance.

21. The method of claim 12 wherein said detection comprises a) separating the target and the photoaptamer to a level sufficient for amplification of the photoaptamer by PCR;

b) amplifying the photoaptamer by PCR; and c) detecting the amplified photoaptamer; whereby the presence or absence of the target molecule in the sample is detected.

22. The method of claim 12 wherein said candidate mixture is prepared by synthesis from a template comprising a region of conserved sequence and a region of randomized and/or biased sequence.

23. The method of claim 12 wherein said candidate mixture comprises nucleic acids each comprising a region of conserved sequence and a region of randomized sequence.

24. A method for measuring the amount of a peptide or protein target molecule in a sample which may contain said target molecule comprising:

a) exposing said sample which may contain said target molecule to a photoaptamer of said target molecule, under conditions wherein a target molecule:photoaptamer complex is formed;

b) irradiating said complex, wherein said target molecule and photoaptamer photocrosslink;

c) determining whether said target molecule:photocrosslink is formed; and d) measuring the amount of the photoaptamer in the sample; whereby the amount of target molecule in the sample may be measured.

25. The method of claim 24 wherein said photoaptamer is a single-stranded nucleic acid ligand.

26. The method of claim 25 wherein said single-stranded nucleic acid ligand is ribonucleic acid.

27. The method of claim 25 wherein said single-stranded nucleic acid ligand is deoxyribonucleic acid.

28. The method of claim 24 wherein said photoaptamer-nucleic acid ligand is labeled.

29. The method of claim 28 wherein said label is a radiolabel.

30. The method of claim 24 wherein said protein is not known to bind nucleic acids as part of its biological function.

31. The method of claim 24 wherein said target molecule is a controlled substance.

32. The method of claim 24 wherein said target molecule is a metabolite.

33. The method of claim 24 wherein said sample is a biological substance.

34. The method of claim 24 wherein said detection is achieved by PCR amplification of said nucleic acid ligand.

35. The method of claim 24 wherein said measurement is qualitative.

36. The method of claim 24 wherein said measurement is quantitative.

37. A method for measuring the amount of a peptide or protein target molecule in a sample which may contain said target molecule comprising:

a) identifying a photoaptamer from a candidate mixture of photoaptamers, said photoaptamer being a ligand of said target molecule, by a method comprising:

i) contacting the candidate mixture with said target molecule, wherein photoaptamers having an increased affinity to said target molecule relative to the candidate mixture form photoaptamer-target complexes;

ii) irradiating said complexes, wherein said target molecule and photoaptamer photocrosslink;

iii) partitioning the crosslinked target molecule and photoaptamer from the remainder of the candidate mixture; and iv) amplifying the crosslinked photoaptamer to yield a ligand-enriched mixture of photoaptamers, whereby an increased affinity photoaptamer may be identified;

b) exposing said sample which may contain said target molecule to said increased affinity photoaptamer of said target molecule under conditions wherein a target molecule:photoaptamer complex is formed;

c) irradiating said complex, wherein said target molecule and photoaptamer photocrosslink;

d) determining whether said target molecule:photoaptamer crosslinked complex is formed; and e) measuring the amount of the photoaptamer in the sample; whereby the amount of target molecule in the sample may be measured.

38. The method of claim 37 further comprising:

iv) repeating steps i), ii), iii) and iv).

39. The method of claim 37 wherein said photoaptamer is a single-stranded nucleic acid ligand.

40. The method of claim 39 wherein said single-stranded nucleic acid ligand is ribonucleic acid.

41. The method of claim 39 wherein said single-stranded nucleic acid ligand is deoxyribonucleic acid.

42. The method of claim 37 wherein said protein is not known to bind nucleic acids as part of its biological function.

43. The method of claim 37 wherein said target molecule is a controlled substance.

44. The method of claim 37 wherein said target molecule is a metabolite.

45. The method of claim 37 wherein said sample is a biological substance.

46. The method of claim 37 wherein said measurement is qualitative.

47. The method of claim 37 wherein said measurement is quantitative.

48. The method of claim 37 wherein said candidate mixture is prepared by synthesis from a template comprising a region of conserved sequence and a region of randomized and/or biased sequence.

49. The method of claim 37 wherein said candidate mixture comprises photoaptamers each comprising a region of conserved sequence and a region of randomized sequence.

* * * * *

SEQUENCE LISTING

<160> NUMBER OF SEQ ID NOS: 100

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(15)
<223> OTHER INFORMATION: All T's are 5-bromouracil

<400> SEQUENCE: 1
gggaggacga tgcgg                                                    15

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(16)
<223> OTHER INFORMATION: All T's are 5-bromouracil

<400> SEQUENCE: 2
tcccgctcgt cgtctg                                                   16

<210> SEQ ID NO 3
<211> LENGTH: 61
<212> TYPE: DNA

```
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil
<221> NAME/KEY: misc_feature
<222> LOCATION: (16)..(45)
<223> OTHER INFORMATION: n is A, C, G, or 5-bromouracil

<400> SEQUENCE: 3
gggaggacga tgcggnnnnn nnnnnnnnnn nnnnnnnnnn nnnnncagac gacgagcggg    60
a                                                                   61

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 4
gggaggacga tgcggtgacg taagagtgta atcgatgcag cctggcagac gacgagcggg    60
a                                                                   61

<210> SEQ ID NO 5
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 5
gggaggacga tgcggtgacg taagagtgta atcgatgcag cctggcagac gacgagcggg    60
a                                                                   61

<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 6
gggaggacga tgcggtgacg taagagtgta atcgatgcag cctggcagac gacgagcggg    60
a                                                                   61

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
```

```
<221> NAME/KEY: modified_base
<222> LOCATION: (1)..(61)
<223> OTHER INFORMATION: All T's are 5-bromouracil

<400> SEQUENCE: 7
gggaggacga tgcggtgacg taagagtgta atcgatgcag cctggcagac gacgagcggg    60
a                                                                   61

<210> SEQ ID NO 8
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 8
gggaggacga tgcggtgacg taagagtgta atcgatgcag cctggcagac gacgagcggg    60
a                                                                   61

<210> SEQ ID NO 9
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 9
gggaggacga tgcggtgacg taagagtgta atcgatgcag cctggcagac gacgagcggg    60
a                                                                   61

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 10
gggaggacga tgcggtgacg taagagtgta atcgatgcag cctggcagac gacgagcggg    60
a                                                                   61

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 11
gggaggacga tgcggtgacg taagagtgta atcgatgcag cctggcagac gacgagcggg    60
``` a                                                             61

<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 12
gggaggacga tgcggaccac agcgctgatg gttcatacta ttccgcagac gacgagcggg     60
a                                                             61

<210> SEQ ID NO 13
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 13
gggaggacga tgcggaccac agcgctgatg gttcatacta ttccgcagac gacgagcggg     60
a                                                             61

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 14
gggaggacga tgcggaccac agcgctgatg gttcatacta ttccgcagac gacgagcggg     60
a                                                             61

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 15
gggaggacga tgcggccaag gtgacatccg ggttcatagt atccgcagac gacgagcggg     60
a                                                             61

<210> SEQ ID NO 16
<211> LENGTH: 61
<212> TYPE: DNA

<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 16
gggaggacga tgcgggccga agtgacacga ggttcatagt atgcccagac gacgagcggg    60
a                                                                   61

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 17
gggaggacga tgcggcgcaa gcaaacgctg agttcatagt atccgcagac gacgagcggg    60
a                                                                   61

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 18
gggaggacga tgcggaccac agcgatgatg gttcatatta ttccacagac gacgagcggg    60
a                                                                   61

<210> SEQ ID NO 19
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 19
gggaggacga tgcggaccac agcgatgatg gttcatatta ttccacagac gacgagcggg    60
a                                                                   61

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 20
gggaggacga tgcgggcgaa gtcattcacg agttcatcat atccccagac gacgagcggg    60
a    61

<210> SEQ ID NO 21
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 21
gggaggacga tgcgggcaaa gttctacgag ttcatcttat cccaacagac gacgagcggg    60
a    61

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 22
gggaggacga tgcgggcaaa gttctacgag ttcatcttat cccaacagac gacgagcggg    60
a    61

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 23
gggaggacga tgcgggcaaa gttctacgag ttcatcttat cccaacagac gacgagcggg    60
a    61

<210> SEQ ID NO 24
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 24
gggaggacga tgcgggccaa gggtctcacg gttcattcta tcccacagac gacgagcggg    60
a    61

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 25
gggaggacga tgcggggcaa gccaacgcgt gttcattgta tcccccagac gacgagcggg    60
a                                                                   61

<210> SEQ ID NO 26
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 26
gggaggacga tgcggcaaag acatactgga ggttcacttt atccgcagac gacgagcggg    60
a                                                                   61

<210> SEQ ID NO 27
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 27
gggaggacga tgcggaccaa agccagcggg ttacatacta tcctgcagac gacgagcggg    60
a                                                                   61

<210> SEQ ID NO 28
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 28
gggaggacga tgcgggtacg aaggcgaccc gagttaatct taccccagac gacgagcggg    60
a                                                                   61

<210> SEQ ID NO 29
<211> LENGTH: 61
<212> TYPE: DNA
<213> ORGANISM: Artificial Sequence
<220> FEATURE:
<223> OTHER INFORMATION: Description of Artificial Sequence: Nucleic

```
       Acid Ligand
<221> NAME/KEY: modified_base
<222> LOCATION: (1)..(61)
<223> OTHER INFORMATION: All T's are 5-bromouracil

<400> SEQUENCE: 29
gggaggacga tgcggacatg aagctactgc gacttaaatc ttggccagac gacgagcggg    60
a                                                                    61

<210> SEQ ID NO 30
<211> LENGTH: 61
<212> TYPE: DNA
<213> ORGANISM: Artificial Sequence
<220> FEATURE:
<223> OTHER INFORMATION: Description of Artificial Sequence: Nucleic
       Acid Ligand
<221> NAME/KEY: modified_base
<222> LOCATION: (1)..(61)
<223> OTHER INFORMATION: All T's are 5-bromouracil

<400> SEQUENCE: 30
gggaggacga tgcgggaaca aaggcgcccg tgtattttct ttccccagac gacgagcggg    60
a                                                                    61

<210> SEQ ID NO 31
<211> LENGTH: 61
<212> TYPE: DNA
<213> ORGANISM: Artificial Sequence
<220> FEATURE:
<223> OTHER INFORMATION: Description of Artificial Sequence: Nucleic
       Acid Ligand
<221> NAME/KEY: modified_base
<222> LOCATION: (1)..(61)
<223> OTHER INFORMATION: All T's are 5-bromouracil

<400> SEQUENCE: 31
gggaggacga tgcgggaaca aaggcgcccg tgtattttct ttccccagac gacgagcggg    60
a                                                                    61

<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Nucleic
       Acid Ligand
<221> NAME/KEY: modified_base
<222> LOCATION: (1)..(55)
<223> OTHER INFORMATION: All T's are 5-bromouracil

<400> SEQUENCE: 32
gggaggacga tgcggcgagc ggagacgttt tattatccac agacgacgag cggga          55

<210> SEQ ID NO 33
<211> LENGTH: 55
<212> TYPE: DNA
<213> ORGANISM: Artificial Sequence
<220> FEATURE:
<223> OTHER INFORMATION: Description of Artificial Sequence: Nucleic
       Acid Ligand
<221> NAME/KEY: modified_base
<222> LOCATION: (1)..(55)
<223> OTHER INFORMATION: All T's are 5-bromouracil

<400> SEQUENCE: 33
gggaggacga tgcggcgagg taggccagtt ttattatcac agacgacgag cggga          55
```

<210> SEQ ID NO 34
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 34
gggaggacga tgcggtgacg taagagtgta atcgatgcag cctggcagac gacgagcggg    60
a                                                                   61

<210> SEQ ID NO 35
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 35
gggaggacga tgcggtgacg taagagtgta atcgatgcag cctggcagac gacgagcggg    60
a                                                                   61

<210> SEQ ID NO 36
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 36
gggaggacga tgcggtgacg taagagtgta atcgatgcag cctggcagac gacgagcggg    60
a                                                                   61

<210> SEQ ID NO 37
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 37
gggaggacga tgcggtgacg taagagtgta atcgatgcag cctggcagac gacgagcggg    60
a                                                                   61

<210> SEQ ID NO 38
<211> LENGTH: 61
<212> TYPE: DNA
<213> ORGANISM: Artificial Sequence
<220> FEATURE:
<223> OTHER INFORMATION: Description of Artificial Sequence: Nucleic Acid Ligand
<221> NAME/KEY: modified_base
<222> LOCATION: (1)..(61)
<223> OTHER INFORMATION: All T's are 5-bromouracil

<400> SEQUENCE: 38
gggaggacga tgcggtgacg taagagtgta atcgatgcag cctggcagac gacgagcggg    60
a                                                                   61

<210> SEQ ID NO 39
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 39
gggaggacga tgcggtgacg taagagtgta atcgatgcag cctggcagac gacgagcggg    60
a                                                                   61

<210> SEQ ID NO 40
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 40
gggaggacga tgcggaccac agcgctgatg gttcatacta ttccgcagac gacgagcggg    60
a                                                                   61

<210> SEQ ID NO 41
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 41
gggaggacga tgcggaccac agcgctgatg gttcatacta ttccgcagac gacgagcggg    60
a                                                                   61

<210> SEQ ID NO 42
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 42
gggaggacga tgcggaccac agcgctgatg gttcatacta ttccgcagac gacgagcggg    60
a    61

<210> SEQ ID NO 43
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 43
gggaggacga tgcggaccac agcgctgatg gttcatacta ttccgcagac gacgagcggg    60
a    61

<210> SEQ ID NO 44
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 44
gggaggacga tgcggcaggc taccacagta ccgagttcat actatcagac gacgagcggg    60
a    61

<210> SEQ ID NO 45
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 45
gggaggacga tgcggcaacc actggggctt gttcatagta tccgccagac gacgagcggg    60
a    61

<210> SEQ ID NO 46
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 46
gggaggacga tgcgggccga atcattgaga gttcatagta tgccccagac gacgagcggg    60
a    61

<210> SEQ ID NO 47
<211> LENGTH: 61

<210> SEQ ID NO 47
<211> LENGTH: 61
<212> TYPE: DNA
<213> ORGANISM: Artificial Sequence
<220> FEATURE:
<223> OTHER INFORMATION: Description of Artificial Sequence: Nucleic
    Acid Ligand
<221> NAME/KEY: modified_base
<222> LOCATION: (1)..(61)
<223> OTHER INFORMATION: All T's are 5-bromouracil

<400> SEQUENCE: 47
gggaggacga tgcggcgaag ggacaaccct acttcataat atccgcagac gacgagcggg    60
a                                                                   61

<210> SEQ ID NO 48
<211> LENGTH: 61
<212> TYPE: DNA
<213> ORGANISM: Artificial Sequence
<220> FEATURE:
<223> OTHER INFORMATION: Description of Artificial Sequence: Nucleic
    Acid Ligand
<221> NAME/KEY: modified_base
<222> LOCATION: (1)..(61)
<223> OTHER INFORMATION: All T's are 5-bromouracil

<400> SEQUENCE: 48
gggaggacga tgcgggccga agttctaacg cgttcatcct atccgcagac gacgagcggg    60
a                                                                   61

<210> SEQ ID NO 49
<211> LENGTH: 61
<212> TYPE: DNA
<213> ORGANISM: Artificial Sequence
<220> FEATURE:
<223> OTHER INFORMATION: Description of Artificial Sequence: Nucleic
    Acid Ligand
<221> NAME/KEY: modified_base
<222> LOCATION: (1)..(61)
<223> OTHER INFORMATION: All T's are 5-bromouracil

<400> SEQUENCE: 49
gggaggacga tgcgggccga agttctaacg cgttcatcct atccgcagac gacgagcggg    60
a                                                                   61

<210> SEQ ID NO 50
<211> LENGTH: 61
<212> TYPE: DNA
<213> ORGANISM: Artificial Sequence
<220> FEATURE:
<223> OTHER INFORMATION: Description of Artificial Sequence: Nucleic
    Acid Ligand
<221> NAME/KEY: modified_base
<222> LOCATION: (1)..(61)
<223> OTHER INFORMATION: All T's are 5-bromouracil

<400> SEQUENCE: 50
gggaggacga tgcgggtcga agccatgcaa gttcattgta tacccagac gacgagcggg     60 a                                                                   61

<210> SEQ ID NO 51
<211> LENGTH: 61
<212> TYPE: DNA
<213> ORGANISM: Artificial Sequence
<220> FEATURE:
<223> OTHER INFORMATION: Description of Artificial Sequence: Nucleic
    Acid Ligand
<221> NAME/KEY: modified_base
<222> LOCATION: (1)..(61)
<223> OTHER INFORMATION: All T's are 5-bromouracil

<400> SEQUENCE: 51
gggaggacga tgcgggtcga agccatgcaa gttcattgta taccccagac gacgagcggg     60
a                                                                    61

<210> SEQ ID NO 52
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 52
gggaggacga tgcggcgaag gtcaccgagt tctatgctat ccgcacagac gacgagcggg     60
a                                                                    61

<210> SEQ ID NO 53
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 53
gggaggacga tgcggcgaag gtcaccgagt tctatgctat ccgcacagac gacgagcggg     60
a                                                                    61

<210> SEQ ID NO 54
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 54
gggaggacga tgcggcgaag gtcaccgagt tctgtgctat ccgcacagac gacgagcggg     60
a                                                                    61

<210> SEQ ID NO 55
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 55
gggaggacga tgcggccgga ggtctccaag ttcattacta tgccacagac gacgagcggg     60
a                                                             61

<210> SEQ ID NO 56
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 56
gggaggacga tgcgggacga aggcgtccga gttcaatctt cccagcagac gacgagcggg    60
a                                                             61

<210> SEQ ID NO 57
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 57
gggaggacga tgcgggacga agacgtgcga gttgaatctt cccagcagac gacgagcggg    60
a                                                             61

<210> SEQ ID NO 58
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 58
gggaggacga tgcgggacga aggcgtccga gttgaatctt cccagcagac gacgagcggg    60
a                                                             61

<210> SEQ ID NO 59
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 59
gggaggacga tgcggccacg aaggcgaccc gagtttcatc ttggccagac gacgagcggg    60
a                                                             61

<210> SEQ ID NO 60
<211> LENGTH: 61
<212> TYPE: DNA
<213> ORGANISM: Artificial Sequence

```
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 60
gggaggacga tgcggccacg aaggcgaccc gagtttcatc ttggccagac gacgagcggg    60
a                                                                   61

<210> SEQ ID NO 61
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 61
gggaggacga tgcgggccga agttctaacg cgtttatcct atgcccagac gacgagcggg    60
a                                                                   61

<210> SEQ ID NO 62
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 62
gggaggacga tgcggcgaaa ggcaacccga gtttatagta tccagcagac gacgagcggg    60
a                                                                   61

<210> SEQ ID NO 63
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 63
gggaggacga tgcgggcgaa ggcacaccga gtttatagta tcccacagac gacgagcggg    60
a                                                                   61

<210> SEQ ID NO 64
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil
```

<400> SEQUENCE: 64
gggaggacga tgcggtgacg taagagtgta atcgatgcag cctggcagac gacgagcggg    60
a                                                                   61

<210> SEQ ID NO 65
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 65
gggaggacga tgcggtgacg taagagtgta atcgatgcag cctggcagac gacgagcggg    60
a                                                                   61

<210> SEQ ID NO 66
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 66
gggaggacga tgcggtgacg taagagtgta atcgatgcag cctggcagac gacgagcggg    60
a                                                                   61

<210> SEQ ID NO 67
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 67
gggaggacga tgcggtgacg taagagtgta atcgatgcag cctggcagac gacgagcggg    60
a                                                                   61

<210> SEQ ID NO 68
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 68
gggaggacga tgcggtgacg taagagtgta atcgatgcag cctggcagac gacgagcggg    60
a                                                                   61

<210> SEQ ID NO 69
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 69
gggaggacga tgcggtgacg taagagtgta atcgatgcag cctggcagac gacgagcggg    60
a                                                                    61

<210> SEQ ID NO 70
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 70
gggaggacga tgcggtgacg taagagtgta atcgatgcag cctggcagac gacgagcggg    60
a                                                                    61

<210> SEQ ID NO 71
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 71
gggaggacga tgcggtgacg taagagtgta atcgatgcag cctggcagac gacgagcggg    60
a                                                                    61

<210> SEQ ID NO 72
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 72
gggaggacga tgcggaccac agcgctgatg gttcatacta ttccacagac gacgagcggg    60
a                                                                    61

<210> SEQ ID NO 73
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand <221> NAME/KEY: modified_base
<222> LOCATION: (1)..(61)
<223> OTHER INFORMATION: All T's are 5-bromouracil

<400> SEQUENCE: 73
gggaggacga tgcggaccac agcgctgatg gttcatacta ttccacagac gacgagcggg    60
a    61

<210> SEQ ID NO 74
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 74
gggaggacga tgcggaccaa aggcaatccg ggttcatact attcccagac gacgagcggg    60
a    61

<210> SEQ ID NO 75
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 75
gggaggacga tgcggaccaa aggcaatccg ggttcatact attcccagac gacgagcggg    60
a    61

<210> SEQ ID NO 76
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 76
gggaggacga tgcgggcgaa ggcacaccga gttcatagta tcccacagac gacgagcggg    60
a    61

<210> SEQ ID NO 77
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 77
gggaggacga tgcgggcgaa ggcacaccga gttcatagta tcccacagac gacgagcggg    60
a                                                                61

<210> SEQ ID NO 78
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 78
gggaggacga tgcgggcgaa ggcacaccga gttcatagta tcccacagac gacgagcggg    60
a                                                                61

<210> SEQ ID NO 79
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 79
gggaggacga tgcggcgcaa gcaaacgctg agttcatagt atccgcagac gacgagcggg    60
a                                                                61

<210> SEQ ID NO 80
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 80
gggaggacga tgcggcgcaa gcaaacgctg agttcatagt atccgcagac gacgagcggg    60
a                                                                61

<210> SEQ ID NO 81
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 81
gggaggacga tgcggggcaa gcgaacgctg agttcatagt atccgcagac gacgagcggg    60
a                                                                61

<210> SEQ ID NO 82
<211> LENGTH: 61
<212> TYPE: DNA

<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 82
gggaggacga tgcggtgacg aaggctaccg agttcatatt attcacagac gacgagcggg    60
a                                                                    61

<210> SEQ ID NO 83
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 83
gggaggacga tgcggcgaag gctacctcca agttcatatt atccgcagac gacgagcggg    60
a                                                                    61

<210> SEQ ID NO 84
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 84
gggaggacga tgcggggcca tgtctcatag ttcatattat acctgcagac gacgagcggg    60
a                                                                    61

<210> SEQ ID NO 85
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 85
gggaggacga tgcggggcca tgtctcatag ttcatattat acctgcagac gacgagcggg    60
a                                                                    61

<210> SEQ ID NO 86
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 86
gggaggacga tgcgggccga agttctaacg cgttcatcct atgcccagac gacgagcggg    60
a    61

<210> SEQ ID NO 87
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 87
gggaggacga tgcgggccga agttctaacg cgttcatcct atgcccagac gacgagcggg    60
a    61

<210> SEQ ID NO 88
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 88
gggaggacga tgcgggccga agttctaacg cgttcatcct atgcccagac gacgagcggg    60
a    61

<210> SEQ ID NO 89
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 89
gggaggacga tgcggcgaag gtcaccgagt tctatgctat ccgcacagac gacgagcggg    60
a    61

<210> SEQ ID NO 90
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 90
gggaggacga tgcggcgaag gtcaccgagt tctatgctat ccgcacagac gacgagcggg    60
a    61

<210> SEQ ID NO 91
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 91
gggaggacga tgcggcgaag gtcaccgagt tctatgctat ccgcacagac gacgagcggg    60
a                                                                    61

<210> SEQ ID NO 92
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 92
gggaggacga tgcggccacg aaggcgaccc gagtttcatc ttggccagac gacgagcggg    60
a                                                                    61

<210> SEQ ID NO 93
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 93
gggaggacga tgcggccacg aaggcgaccc gagtttcatc ttggccagac gacgagcggg    60
a                                                                    61

<210> SEQ ID NO 94
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 94
gggaggacga tgcggccacg aaggcgaccc gagtttcatc ttggccagac gacgagcggg    60
a                                                                    61

<210> SEQ ID NO 95
<211> LENGTH: 61
<212> TYPE: DNA
<213> ORGANISM: Artificial Sequence
<220> FEATURE:
<223> OTHER INFORMATION: Description of Artificial Sequence: Nucleic -continued

```
    Acid Ligand
<221> NAME/KEY: modified_base
<222> LOCATION: (1)..(61)
<223> OTHER INFORMATION: All T's are 5-bromouracil

<400> SEQUENCE: 95
gggaggacga tgcggccacg aaggcgaccc gagtttcatc ttggccagac gacgagcggg    60
a                                                                   61

<210> SEQ ID NO 96
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 96
gggaggacga tgcgggacga aggcgcccga gttgaatctt cccagcagac gacgagcggg    60
a                                                                   61

<210> SEQ ID NO 97
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: ()..()
<223> OTHER INFORMATION: All T's are 5-bromouracil

<400> SEQUENCE: 97
gggaggacga tgcgggacga aggcgcccga gttgaatctt cccagcagac gacgagcggg    60
a                                                                   61

<210> SEQ ID NO 98
<211> LENGTH: 61
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(61)
<223> OTHER INFORMATION: All T's are 5-bromouracil

<400> SEQUENCE: 98
gggaggacga tgcgggacga aggcgcccga gttgaatctt cccagcagac gacgagcggg    60
a                                                                   61

<210> SEQ ID NO 99
<211> LENGTH: 155
<212> TYPE: PRT
<213> ORGANISM: Homo sapiens

<400> SEQUENCE: 99

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
            20                  25                  30
```

-continued

```
Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 100
<211> LENGTH: 13
<212> TYPE: DNA
<213> ORGANISM: Artificial Sequence
<220> FEATURE:
<223> OTHER INFORMATION: Description of Artificial Sequence: Nucleic
      Acid Ligand
<221> NAME/KEY: modified_base
<222> LOCATION: (1)..(13)
<223> OTHER INFORMATION: All T's are 5-bromouracil

<400> SEQUENCE: 100
ggactagtca aac                                                      13
```